US011397594B1

(12) United States Patent
David et al.

(10) Patent No.: US 11,397,594 B1
(45) Date of Patent: Jul. 26, 2022

(54) DYNAMIC LOADING OF AN EXTENDING APPLICATION

(71) Applicant: VIM INC., San Francisco, CA (US)

(72) Inventors: Asaf David, Tel Aviv (IL); Nicolas Mendzylewski, Tel Aviv (IL); Moran Shemesh, Tel Aviv (IL); Chen Rozenes, Tel Aviv (IL)

(73) Assignee: VIM INC., San Francisco, CA (US)

( * ) Notice: Subject to any disclaimer, the term of this patent is extended or adjusted under 35 U.S.C. 154(b) by 0 days.

(21) Appl. No.: 17/540,711

(22) Filed: Dec. 2, 2021

Related U.S. Application Data

(63) Continuation of application No. 17/502,567, filed on Oct. 15, 2021.

(51) Int. Cl.
*G06F 9/445* (2018.01)
*G06F 21/62* (2013.01)

(52) U.S. Cl.
CPC ...... *G06F 9/44521* (2013.01); *G06F 21/6281* (2013.01)

(58) Field of Classification Search
CPC .................. G06F 9/44521; G06F 21/6281
See application file for complete search history.

(56) References Cited

U.S. PATENT DOCUMENTS

| 4,782,384 | A | * | 11/1988 | Tucker | .................... | H04N 9/11 |
| | | | | | | 348/E9.037 |
| 8,799,988 | B2 | * | 8/2014 | Conlan | ................ | G06F 21/606 |
| | | | | | | 726/1 |
| 9,274,913 | B2 | * | 3/2016 | Kay | .................... | G06F 11/3093 |
| 2013/0297973 | A1 | * | 11/2013 | Hyland | ................... | G06F 11/28 |
| | | | | | | 714/27 |
| 2020/0242186 | A1 | * | 7/2020 | Yang | ....................... | G06F 16/93 |

* cited by examiner

*Primary Examiner* — Umut Onat
*Assistant Examiner* — Phuong N Hoang
(74) *Attorney, Agent, or Firm* — Myers Wolin, LLC

(57) ABSTRACT

An apparatus, system and product including a software agent configured to monitor and interact with a Document Object Model (DOM) of a page of an Electronic Health Record (EHR) system; a runtime infrastructure that is loaded, dynamically, in the page in a first iframe; an EHR-specific EHR adapter that is loaded, dynamically, in the page; and an extending application that is loaded, dynamically, in the page in a second iframe, wherein the EHR-specific EHR adapter is configured to receive EHR-specific instructions from the software agent and communicate converted cross-EHR instructions to the runtime infrastructure, wherein the runtime infrastructure is configured to communicate the converted cross-EHR instructions to the extending application and receive cross-EHR instructions from the extending application, wherein the EHR-specific EHR adapter is configured to obtain the cross-EHR instructions and communicate converted EHR-specific instructions to the software agent.

20 Claims, 6 Drawing Sheets

DYNAMIC LOADING OF AN EXTENDING APPLICATION

CROSS-REFERENCE TO RELATED APPLICATION

This application is a continuation of U.S. patent application Ser. No. 17/502,567, filed on Oct. 15, 2021, which is hereby incorporated by reference in its entirety without giving rise to disavowment.

TECHNICAL FIELD

The present disclosure relates to loading of applications in general, and to dynamically loading applications over a data system, in particular.

BACKGROUND

One or more software modules may be used in order to customize a user's display. For example, a browser extension may comprise a small software module for customizing a web browser, a webpage, or the like. Browsers typically allow a variety of extensions to perform user interface modifications, ad blocking, and cookie management.

In some cases, a user display may present an interface of one or more Electronic Health Record (EHR) systems, also referred to as Electronic Medical Records (EMRs), which may comprise records of medical data of a patient in a digital version. An EHR may contain Protected Health Information (PHI) such as the medical and treatment histories of patients. Under the US law, PHI information may comprise any information about health status, provision of health care, or payment for health care that is created or collected by a covered entity (or a business associate of a covered entity), and can be linked to a specific individual. This may be interpreted broadly to include any part of a patient's medical record or payment history.

BRIEF SUMMARY

One exemplary embodiment of the disclosed subject matter is an apparatus comprising: a software agent configured to monitor and interact with a Document Object Model (DOM) of a page of an Electronic Health Record (EHR) system; a runtime infrastructure that is loaded, dynamically, in the page of the EHR system in a first iframe; an EHR-specific EHR adapter that is loaded, dynamically, in the page of the EHR system; and an extending application that is loaded, dynamically, in the page of the EHR system in a second iframe, wherein the EHR-specific EHR adapter is specifically designed based on the EHR system, wherein the EHR-specific EHR adapter is configured to receive EHR-specific instructions from the software agent and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the software agent, wherein said apparatus is configured to implement a functionality that is not provided by the EHR system at least by: monitoring, by the software agent, for an event in the EHR system; notifying, by the software agent, the EHR-specific EHR adapter of the event via an EHR-specific instruction; translating, by the EHR-specific EHR adapter, the EHR-specific instruction to a converted cross-EHR instruction that is provided to the extending application via the runtime infrastructure; executing, by the extending application, a cross-EHR business logic in response to the converted cross-EHR instruction to determine a cross-EHR response; and translating, by the EHR-specific EHR adapter, the cross-EHR response to a converted EHR-specific instruction that can be implemented by the software agent over the EHR system.

Optionally, the runtime infrastructure lacks a Graphical User Interface (GUI) representation.

Optionally, the extending application comprises a GUI component, and the business logic is configured to manipulate the GUI component.

Optionally, the extending application is an automation process that lacks a GUI representation.

Optionally, the runtime infrastructure is configured to: retrieve from a server a list of applications to be loaded in the page comprising at least the extending application, wherein the runtime infrastructure is configured to dynamically load the extending application in the second iframe by provisioning a Uniform Resource Locator (URL) to be loaded in the second iframe, wherein the URL is pointing to a code of the extending application, whereby the apparatus is enabled to load new code and provision new functionality by changing the code or changing the URL without changing the software agent, whereby the apparatus prevents a dynamic execution of a string representing client-side code.

Optionally, the list of applications to be loaded is determined based on access permissions of a user of the EHR system to applications in an application repository.

Optionally, the software agent is configured to inject the first iframe in the page of the EHR system and cause the runtime infrastructure to be loaded into the first iframe.

Optionally, the software agent is configured to inject the second iframe in the page of the EHR system and enable the runtime infrastructure to load the extending application into the second iframe.

Optionally, the cross-EHR response is configured to perform a User Interface (UI) manipulation in the page of the EHR system or a data update in the page of the EHR system.

Optionally, the software agent is configured to inject the EHR-specific EHR adapter in the page of the EHR system and load the EHR-specific EHR adapter.

Optionally, the software agent comprises a browser extension that is configured to be executed by a browser, wherein the browser is configured to render the page of the EHR system.

Optionally, the software agent comprises a desktop agent, wherein the EHR system comprises a desktop-based EHR system, wherein the desktop agent is configured to be executed over the desktop-based EHR system.

Optionally, the runtime infrastructure is configured to retrieve from a server a list of applications to be loaded in the page, wherein the list of applications to be loaded comprises the extending application and a second application, wherein the extending application belongs to a first organization associated with a first server, wherein the second application belongs to a second organization associated with a second server, wherein the runtime infrastructure is configured to dynamically load the second application in a third iframe embedded in the page by provisioning a URL to be loaded in the third iframe, wherein the URL is pointing to a code of the second application.

Optionally, the runtime infrastructure is configured to retrieve from a server a list of applications to be loaded in the page, wherein the list of applications to be loaded comprises the extending application and a second application, wherein the extending application belongs to a first organization associated with a first server, wherein the second application belongs to a second organization associated with a second server, wherein the runtime infrastructure is configured to dynamically load the second application in the second iframe by provisioning a URL of the second application to be loaded in the second iframe, wherein the URL of the second application is pointing to a code of the second application, wherein the URL of the second application replaces a URL of the extending application.

Optionally, the runtime infrastructure is configured to dynamically load the second application in the second iframe in response to a second event.

Optionally, the list of applications is available in a marketplace, wherein any provider is enabled to upload a new application to the marketplace, wherein a user of the EHR system is enabled to install in a user device any application from the marketplace.

Optionally, the EHR-specific EHR adapter is configured to indicate to the software agent an element of interest via an indication, wherein the software agent is configured to monitor the element of interest in response to the indication, wherein the software agent is configured to notify the EHR-specific EHR adapter of the EHR-specific instruction in response to monitoring the event, wherein the event is associated to the element of interest.

Optionally, the software agent is configured to inject the first and second iframes in response to determining that the extending application is configured to be loaded over the page of the EHR system.

Another exemplary embodiment of the disclosed subject matter is a system comprising: a software agent configured to monitor and interact with a DOM of a page of an EHR system; a runtime infrastructure that is loaded, dynamically, in the page of the EHR system in a first iframe; an EHR-specific EHR adapter that is loaded, dynamically, in the page of the EHR system; and an extending application that is loaded, dynamically, in the page of the EHR system in a second iframe, wherein the EHR-specific EHR adapter is specifically designed based on the EHR system, wherein the EHR-specific EHR adapter is configured to receive EHR-specific instructions from the software agent and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the software agent, wherein said system is configured to implement a functionality that is not provided by the EHR system at least by: monitoring, by the software agent, for an event in the EHR system; notifying, by the software agent, the EHR-specific EHR adapter of the event via an EHR-specific instruction; translating, by the EHR-specific EHR adapter, the EHR-specific instruction to a converted cross-EHR instruction that is provided to the extending application via the runtime infrastructure; executing, by the extending application, a cross-EHR business logic in response to the converted cross-EHR instruction to determine a cross-EHR response; and translating, by the EHR-specific EHR adapter, the cross-EHR response to a converted EHR-specific instruction that can be implemented by the software agent over the EHR system.

Yet another exemplary embodiment of the disclosed subject matter is a computer program product comprising a non-transitory computer readable medium retaining program instructions, which program instructions when read by a processor, cause the processor to: obtain a software agent configured to monitor and interact with a DOM of a page of an EHR system; obtain a runtime infrastructure that is loaded, dynamically, in the page of the EHR system in a first iframe; obtain an EHR-specific EHR adapter that is loaded, dynamically, in the page of the EHR system; and obtain an extending application that is loaded, dynamically, in the page of the EHR system in a second iframe, wherein the EHR-specific EHR adapter is specifically designed based on the EHR system, wherein the EHR-specific EHR adapter is configured to receive EHR-specific instructions from the software agent and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the software agent, wherein said processor is configured to implement a functionality that is not provided by the EHR system at least by: monitoring, by the software agent, for an event in the EHR system; notifying, by the software agent, the EHR-specific EHR adapter of the event via an EHR-specific instruction; translating, by the EHR-specific EHR adapter, the EHR-specific instruction to a converted cross-EHR instruction that is provided to the extending application via the runtime infrastructure; executing, by the extending application, a cross-EHR business logic in response to the converted cross-EHR instruction to determine a cross-EHR response; and translating, by the EHR-specific EHR adapter, the cross-EHR response to a converted EHR-specific instruction that can be implemented by the software agent over the EHR system.

Yet another exemplary embodiment of the disclosed subject matter is an apparatus comprising: a browser extension configured to monitor and interact with a DOM of a page of an EHR system, wherein the browser extension is configured to be executed by a browser, wherein the browser is configured to render the page of the EHR system; a runtime infrastructure that is loaded, dynamically, in the page of the EHR system in a first iframe, wherein the runtime infrastructure lacks a GUI representation; an EHR-specific EHR adapter that is loaded, dynamically, in the page of the EHR system; and an extending application that is loaded, dynamically, in the page of the EHR system in a second iframe, wherein the browser extension is configured to inject the first iframe in the page of the EHR system and cause the runtime infrastructure to be loaded into the first iframe, wherein the browser extension is configured to inject the second iframe in the page of the EHR system and enable the runtime infrastructure to load the extending application into the second iframe, wherein the EHR-specific EHR adapter is specifically designed based on the EHR system, wherein the EHR-specific EHR adapter is configured to receive EHR-specific instructions from the browser extension and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the browser extension, wherein said apparatus is configured to implement a functionality that is not provided by the EHR system at least by: monitoring, by the browser extension, for an event in the EHR system; notifying, by the browser extension, the EHR-specific EHR adapter of the event via an EHR-specific instruction; translating, by the EHR-specific EHR adapter, the EHR-specific instruction to a converted cross-EHR instruction that is provided to the extending application via the runtime infrastructure; executing, by the extending application, a cross-EHR business logic in response to the converted cross-EHR instruction to determine a cross-EHR response; and translating, by the EHR-specific EHR adapter, the cross-EHR response to a converted EHR-specific instruction that can be implemented by the browser extension over the EHR system.

Optionally, the extending application comprises a GUI component, wherein the business logic is configured to manipulate the GUI component.

Optionally, the extending application is an automation process, wherein the automation process lacks a GUI representation.

Optionally, the runtime infrastructure is configured to: retrieve from a server a list of applications to be loaded in the page, wherein the list of applications to be loaded comprises at least the extending application, wherein the runtime infrastructure is configured to dynamically load the extending application in the second iframe by provisioning a URL to be loaded in the second iframe, wherein the URL is pointing to a code of the extending application, whereby the apparatus is enabled to load new code and provision new functionality by changing the code or changing the URL without changing the browser extension, whereby the apparatus prevents a dynamic execution of a string representing client-side code.

Optionally, the list of applications to be loaded is determined based on access permissions of a user of the EHR system to applications in an application repository.

Optionally, the cross-EHR response is configured to perform a UI manipulation in the page of the EHR system or a data update in the page of the EHR system.

Optionally, the browser extension is configured to inject the EHR-specific EHR adapter in the page of the EHR system and load the EHR-specific EHR adapter.

Optionally, the runtime infrastructure is configured to retrieve from a server a list of applications to be loaded in the page, wherein the list of applications to be loaded comprises the extending application and a second application, wherein the extending application belongs to a first organization associated with a first server, wherein the second application belongs to a second organization associated with a second server, wherein the runtime infrastructure is configured to dynamically load the second application in a third iframe embedded in the page by provisioning a URL to be loaded in the third iframe, wherein the URL is pointing to a code of the second application.

Optionally, the runtime infrastructure is configured to retrieve from a server a list of applications to be loaded in the page, wherein the list of applications to be loaded comprises the extending application and a second application, wherein the extending application belongs to a first organization associated with a first server, wherein the second application belongs to a second organization associated with a second server, wherein the runtime infrastructure is configured to dynamically load the second application in the second iframe by provisioning a URL of the second application to be loaded in the second iframe, wherein the URL of the second application is pointing to a code of the second application, wherein the URL of the second application replaces a URL of the extending application.

Optionally, the runtime infrastructure is configured to dynamically load the second application in the second iframe in response to a second event.

Optionally, a list of applications is available in a marketplace, wherein any provider is enabled to upload a new application to the marketplace, wherein a user of the EHR system is enabled to install in a user device any application from the marketplace.

Optionally, the EHR-specific EHR adapter is configured to indicate to the browser extension an element of interest via an indication, wherein the browser extension is configured to monitor the element of interest in response to the indication, wherein the browser extension is configured to notify the EHR-specific EHR adapter of the EHR-specific instruction in response to monitoring the event, wherein the event is associated to the element of interest.

Optionally, the browser extension is configured to inject the first and second iframes in response to determining that the extending application is configured to be loaded over the page of the EHR system.

Yet another exemplary embodiment of the disclosed subject matter is a system comprising: a browser extension configured to monitor and interact with a DOM of a page of an EHR system, wherein the browser extension is configured to be executed by a browser, wherein the browser is configured to render the page of the EHR system; a runtime infrastructure that is loaded, dynamically, in the page of the EHR system in a first iframe, wherein the runtime infrastructure lacks a GUI representation; an EHR-specific EHR adapter that is loaded, dynamically, in the page of the EHR system; and an extending application that is loaded, dynamically, in the page of the EHR system in a second iframe, wherein the browser extension is configured to inject the first iframe in the page of the EHR system and cause the runtime infrastructure to be loaded into the first iframe, wherein the browser extension is configured to inject the second iframe in the page of the EHR system and enable the runtime infrastructure to load the extending application into the second iframe, wherein the EHR-specific EHR adapter is specifically designed based on the EHR system, wherein the EHR-specific EHR adapter is configured to receive EHR-specific instructions from the browser extension and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the browser extension, wherein said system is configured to implement a functionality that is not provided by the EHR system at least by: monitoring, by the browser extension, for an event in the EHR system; notifying, by the browser extension, the EHR-specific EHR adapter of the event via an EHR-specific instruction; translating, by the EHR-specific EHR adapter, the EHR-specific instruction to a converted cross-EHR instruction that is provided to the extending application via the runtime infrastructure; executing, by the extending application, a cross-EHR business logic in response to the converted cross-EHR instruction to determine a cross-EHR response; and translating, by the EHR-specific EHR adapter, the cross-EHR response to a converted EHR-specific instruction that can be implemented by the browser extension over the EHR system.

Yet another exemplary embodiment of the disclosed subject matter is a computer program product comprising a non-transitory computer readable medium retaining program instructions, which program instructions when read by a processor, cause the processor to: monitor and interact with a DOM of a page of an EHR system using a browser extension, wherein the browser extension is configured to be executed by a browser, wherein the browser is configured to render the page of the EHR system; dynamically load a runtime infrastructure in the page of the EHR system in a first iframe, wherein the runtime infrastructure lacks a GUI representation; dynamically load an EHR-specific EHR adapter in the page of the EHR system; and dynamically load an extending application in the page of the EHR system in a second iframe, wherein the browser extension is configured to inject the first iframe in the page of the EHR system and cause the runtime infrastructure to be loaded into the first iframe, wherein the browser extension is configured to inject the second iframe in the page of the EHR system and enable the runtime infrastructure to load the extending application into the second iframe, wherein the EHR-specific EHR adapter is specifically designed based on the EHR system, wherein the EHR-specific EHR adapter is configured to receive EHR-specific instructions from the browser extension and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the browser extension, wherein said processor is configured to implement a functionality that is not provided by the EHR system at least by: monitoring, by the browser extension, for an event in the EHR system; notifying, by the browser extension, the EHR-specific EHR adapter of the event via an EHR-specific instruction; translating, by the EHR-specific EHR adapter, the EHR-specific instruction to a converted cross-EHR instruction that is provided to the extending application via the runtime infrastructure; executing, by the extending application, a cross-EHR business logic in response to the converted cross-EHR instruction to determine a cross-EHR response; and translating, by the EHR-specific EHR adapter, the cross-EHR response to a converted EHR-specific instruction that can be implemented by the browser extension over the EHR system.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
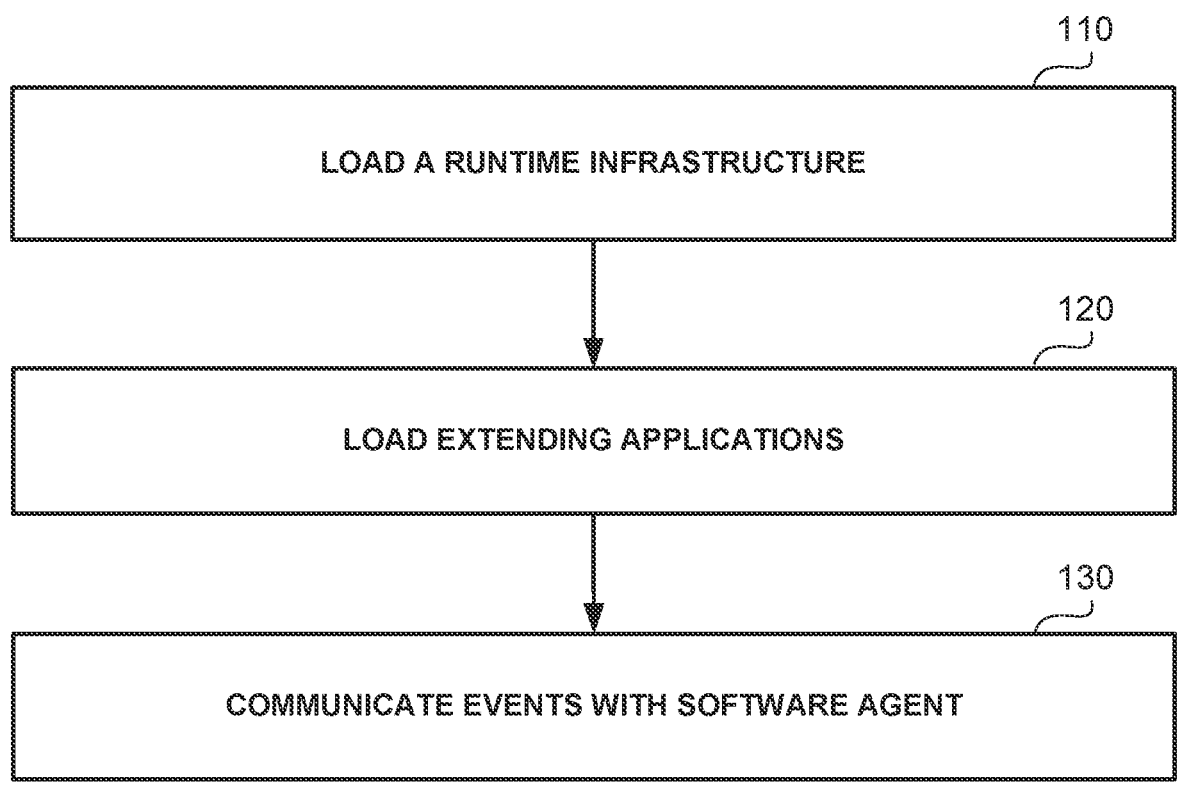
FIG. 1 illustrates a flowchart diagram of a method, in accordance with some exemplary embodiments of the disclosed subject matter.

One technical problem dealt with by the disclosed subject matter is enabling an extending service to extend a functionality or content of a browsed page, e.g., by pushing additional content to the page, loading resources thereto, or the like. In some exemplary embodiments, the browsed page may be associated with a data system that may retain data records of one or more users. In some exemplary embodiments, a plurality of separate data systems may retain other records of overlapping users, e.g., with different or overlapping user information.

In some exemplary embodiments, the data systems may comprise, in some scenarios, Electronic Health Record (EHR) systems, and the browsed page may comprise a page of an EHR system. In some exemplary embodiments, EHRs, also referred to as Electronic Medical Records (EMRs), may comprise records of medical data of a patient in a digital version. In some exemplary embodiments, an EHR may contain the medical and treatment histories of patients, and may be accessed via various interfaces such as EHR software systems which may comprise desktop applications, websites, or the like. In some exemplary embodiments, separate EHR systems may retain data that is not synchronized with other EHR systems, data centers, or the like, such as regarding a same subject.

In some exemplary embodiments, EHR systems may be used by various actors or entities such as a payer entity, a covered entity, a provider entity, a patient, or the like. In some exemplary embodiments, a payer may comprise a health insurance entity, an entity that assumes the risk of paying for medical treatments, or the like. In some exemplary embodiments, a provider may comprise doctors, Primary Care Physicians (PCPs), clinics, or the like, e.g., which may be supported by one or more payers. In some exemplary embodiments, a covered entity may comprise an entity who provides treatment, payment and operations in healthcare such as a doctor's office, dental offices, clinics, psychologists, nursing homes, pharmacies, hospitals or home healthcare agencies, health plans, insurance companies, Health Maintenance Organizations (HMOs), or the like. In some exemplary embodiments, separate EHR systems may be used by different providers, different payers, different covered entities, or the like, each system thereof may retain different data records of a same patient.

In some exemplary embodiments, EHR systems of any entity may retain a database or repository that comprises sensitive medical data, such as Protected health information (PHI). In some exemplary embodiments, PHI information may comprise data about a health status, provision of health care, payment for health care, or the like, that is created or collected by a covered entity, and can be linked to a specific individual. In some exemplary embodiments, government regulations, privacy treaties, privacy concerns, or the like, may impose one or more privacy restrictions on EHR systems. In some exemplary embodiments, EHR systems may be required to comply with government regulations or protocols, such as the Fast Healthcare Interoperability Resources (FHIR) standard created by the Health Level Seven International (HL7) health-care standards organization, which comprises a permitted Application Programming Interface (API) for exchanging EHR records. In some exemplary embodiments, government regulations, as well as privacy concerns, may prohibit unrelated parties from accessing PHI information of a patient, such as a patient's medical record or payment history. In some exemplary embodiments, this may prevent an EHR system that is used on behalf of a patient from accessing data of the same patient that is retained in a separate EHR system, even if such information is crucial for providing medical care to the patient. Additionally, as EHR systems may comprise sensitive and protected data, which may limit data sharing protocols.

In some exemplary embodiments, EHR systems that do not share with each other data about a shared patient may have one or more drawbacks for the patient. For example, in case an EHR system of a patient's payer and an EHR system of the patient's provider are prevented from sharing the patient's data, or do not share such data for any other reason, the provider may not know about the history, conditions, or the like, of the patient, which may be determined by the payer. As another example, in case separate EHR systems that retain data records of the patient are prevented from sharing the patient's data with each other, the user may use a first EHR system without having access to medical recommendations from the second EHR system, the user may be provided with an incorrect diagnosis at the first EHR system as the relevant medical information may be retained at the second EHR system, or the like, e.g., which may be life threatening in some cases. In some exemplary embodiments, prohibiting EHR systems from sharing with each other data about a shared patient may have one or more drawbacks for the payer, as the payer may not have sufficient information to estimate an overall medical state of the patient. It may be desired to correlate user information over different EHR systems, without violating any privacy regulations or concerns.

In some exemplary embodiments, it may be desired to provide an extending service for extending a Graphical User Interface (UI) (GUI) of an EHR system with extending applications such as additional data, functionalities, or the like, that are not available in the EHR system but can be obtained or derived from different EHR systems. For example, it may be desired to push additional content to a browsed EHR page, load resources thereto, or the like.

A naïve solution for loading extending applications over an EHR system may include modifying the EHR system to include the extending applications within the system. The naïve solution may have one or more drawbacks. In some exemplary embodiments, modifying each EHR system separately, may not be scalable when dealing with a large number of EHR systems, e.g., hundreds of EHR systems. In some exemplary embodiments, modifying all of the EHR systems independently may be resource consuming, time consuming, or the like.

A second naïve solution to the drawbacks of modifying each EHR system independently, may include utilizing dynamic loading of code to load extending applications. In some exemplary embodiments, a client-side agent may be configured to dynamically load code of a functionality that is to be augmented to an EHR system, by fetching the code from a backend server and activating the code. In some exemplary embodiments, this solution may overcome the drawbacks of modifying each EHR system independently, at least since dynamic loading of code can be cross-EHR, and may be performed for multiple EHR systems. For example, the code of the functionality may be obtained in the form of a string, and the code may be activated such as by using an "eval" JavaScript command to execute the string, or by using any other activating command. The second naïve solution for dynamically loading code of a functionality may have one or more drawbacks. In some exemplary embodiments, fetching and activating code may introduce the risk that the code might be manipulated by an adversary, which may damage the hosting EHR system over which the code is executed, may damage a backend thereof, may damage the augmenting entity that fetches and activates the code, or the like.

Another technical problem dealt with by the disclosed subject matter is enabling an extending service to augment functionalities over multiple data systems, e.g., in a secure manner, while overcoming the drawbacks of the naïve solution.

Yet another technical problem dealt with by the disclosed subject matter is to provide users with a smooth and seamless integration of augmented applications with the EHR system that is being used, while enabling the extending applications to push valuable content on to a user's workflow. For example, it may be desired that the extending service will be enabled to monitor the browsed page and provide an extending application such as recommendations of doctors that are being searched for, without adversely affecting the user's workflow in the EHR system.

Yet another technical problem dealt with by the disclosed subject matter is enabling third party unauthorized entities, that are not authorized to access sensitive data, to provide an augmented functionality that is intended to be executed over the EHR systems in certain scenarios, without exposing any sensitive data of users to the unauthorized entities. For example, a third party entity may desire to provide recommendations of a list of providers that are covered by a payer of the user, without being exposed to the list or to any PHI information.

Yet another technical problem dealt with by the disclosed subject matter is executing an extending application over the EHR system and enabling it to push content to a browsed EHR page, load resources thereto, or the like, in case the content that is added to the browsed EHR page is allowed to be exposed to the user consuming the browsed EHR page, and without exposing sensitive user data to unauthorized entities.

It is noted that the disclosed subject matter is exemplified with relation to different EHR systems that do not share data, but it is not limited to the medical realm or to EHR systems specifically. As an example, the disclosed subject matter may be applied to any other data-retaining systems. In some exemplary embodiments, the EHR systems that are described herein may comprise any software systems that retain records of data of a same subject without being enabled or configured to directly share the data with each other. For example, the systems may comprise two separate systems for retaining résumés, both retaining a résumé of a same applicant without enabling each other to share her retained résumé. Alternatively, the data that is retained at the systems may not relate to a human subject but to any other subject, object, topic, or the like.

One technical solution provided by the disclosed subject matter is providing an architecture comprising a software agent such as a browser extension and runtime infrastructure that are associated with an extending service, provided thereby, or the like. In some exemplary embodiments, the extending service may be configured to accumulate EHR-related data from multiple EHR systems over which extending applications may be executed, such as payer systems, provider systems, covered systems, or the like. The extending service may retain a storage of data records at a server or any other computing device that is independent from the EHR systems, from the payer systems, from the provider systems, or the like. In some exemplary embodiments, the storage of the extending service may retain user accounts, user records, data records from payer and provider entities, data regarding providers, data regarding covered entities, data regarding payers, accumulate data from interfaces of EHR systems, or the like, which may enable extending applications to augment new functionalities over EHR systems.

In some exemplary embodiments, the extending service may be configured to execute one or more extending applications over EHR systems that are being used by a patient or on behalf of the patient. For example, upon logging in to an EHR system, the extending service may automatically identify the logging in process of the patient, scrape her credentials, and log the user into her account of the extending service, which may be independent from the EHR system, and execute one or more extending applications over the EHR pages that are browsed by the user. In some exemplary embodiments, an extending application of the extending service may be configured to push additional content to an EHR page, load resources thereto, manipulate GUI elements, provide data or functionalities to the EHR page, or the like. In some exemplary embodiments, the storage of the extending service may enable a user browsing an EHR session to utilize functionalities that are derived from different systems such as a payer entity, a provider entity, a covered entity, a separate EHR system of a same type of entity, a combination thereof, or the like.

In some exemplary embodiments, the extending service may distribute one or more software agents to local memories of user devices, provider computers, payer systems, or the like. In some exemplary embodiments, an agent may comprise a software module such as a browser extension, which may be executed by a browser rendering the EHR system. Alternatively, an agent may comprise a software module such as a Software Development Kit (SDK) or Dynamic-Link Library (DLL) files in the disk memory that may be executed over a desktop EHR system. In some exemplary embodiments, in case of a desktop agent, the agent may be located or retained in EHR executables of the of the desktop EHR system, in Operating System (OS) executables, adjacently to the installation or address of the associated EHR system, or the like. In some exemplary embodiments, in case the EHR executables of the of the desktop EHR system are located in a virtual machine, a desktop designated agent may be deployed in the virtual machine, from which the agent may receive updates regarding the EHR system.

In some exemplary embodiments, an agent may be utilized to monitor the user interface of the EHR system, the Document Object Model (DOM) thereof, hooks thereof, events thereof, or the like, and to dynamically load one or more extending applications over the executing EHR system. In some exemplary embodiments, the extending applications may be configured to provide additive functionalities, data, a combination thereof, or the like, that may be added to or embedded in the EHR page of the EHR system. For example, an extending application may be configured to add or manipulate a GUI element in the page, such as in order to enable the user to perform a functionality such as booking a treatment that was not enabled prior to executing the extending application.

In some exemplary embodiments, an agent (also referred to as the "extension") may be configured to conduct communications with the backend of the extending service, e.g., to obtain an EHR adapter to an underlying EHR system that is being used by the user, to obtain extending applications therefrom, to enhance a security of a user session, or the like. In some exemplary embodiments, the agent may be configured to augment EHR systems with one or more extending applications comprising software layers that can be executed over the EHR system. In some exemplary embodiments, the extending applications may be loaded in one or more Inline Frames (iframes) that may be managed by the EHR adapter. In some exemplary embodiments, prior to augmenting EHR systems with one or more extending applications, the agent may verify that a domain of the underlying system comprises a domain for which the agent is configured, e.g., a domain of an EHR system. For example, the agent may retain a list of domains of EHR systems, and compare the domains to a domain of a rendered page, prior to attempting to augment an extending application thereover.

In some exemplary embodiments, the agent may be configured to monitor an EHR display of the user, such as in response to an instruction of an EHR adapter that is loaded over the page, and accumulate information therefrom, which may or may not be added to a storage in the backend of the extending service. In some exemplary embodiments, the agent may provide facilities for an extending application to provide its functionality over the display of the user, such as by injecting iframes that enable extending applications to be loaded therein, retrieving extending applications from the server such as based on the monitored display of the user, or the like. In some exemplary embodiments, the extending application may utilize the agent's facilities, such as the iframe, in order to load functionalities from the backend of the extending service. In some exemplary embodiments, the browser extension may be configured to monitor the user's display, monitor the EHR user interface, track cursor and keyboard activity, or the like, and identify browser events. In some exemplary embodiments, the extension may be configured to access a DOM or any other representation of the browsed EHR pages such as via hooks, API calls, or the like, and communicate with the EHR adapter therein. In some exemplary embodiments, the extension may obtain event data or page data by monitoring the page, subscribing to events within the page, monitoring network traffic, using Windows™ API calls or any other API calls, performing dynamic injection of DLLs, or the like. In some exemplary embodiments, the extension may be configured to inform one or more iframes of any detected browser events.

In some exemplary embodiments, the extending applications may be configured to push content and resources over a page, and may be loaded in iframes that may be generated or injected by the browser extension or another monitoring agent that is executed at the client-side. The extending applications may provide the user with additional medical options, additional medical data, additional semi-medical data, or the like. In some cases, extending applications may be configured to insert a widget into the DOM, manipulate a widget, re-launch a window, or the like. In some exemplary embodiments, an extending application may comprise an automation code such as a Robotic Process Automation (RPA) embedded within an iframe that is not visible, has no GUI, or the like, while the code may automatically interact with the EHR system and modify properties thereof, change its behavior, or the like. For example, an automation code may be configured to enable the user to book a treatment at a provider that is not available via the EHR system, which may be activated from a remote backend.

The extending applications may comprise cross-EHR applications that are not specifically tailored for a specific EHR system, but are rather configured to be executed over various different EHR systems that are not related or associated with each other or with the extending service, that are not enabled to access each other, that belong to different entities, or the like. The extending applications may enable to indicate to a first active EHR system, medical information or functionalities that are derived from a second EHR system to which the first EHR system has no access, that are derived from a server of a payer to which the first EHR system has no access, that are derived from a server of a covered entity to which the first EHR system has no access, or the like. The medical information or functionalities that is indicated to the first EHR system may only include data to which the first EHR system has permission to access, is authorized to access, or the like. In some cases, an extending application loaded in an iframe may enable separate EHR systems to share data with each other indirectly, possibly unintentionally, and to provide augmented applications that can enrich the medical options, augment the EHR system's display with additional data, or the like, thereby enhancing a workflow of the user. In some exemplary embodiments, the augmented applications may comprise, for example, recommendations of providers that are supported by the payer, scores of doctors based on selected parameters such as cost and quality, scores that are obtained from the payer's system, scores of doctors based on processing data at the extending service, or the like.

In some exemplary embodiments, the EHR adapter may obtain from a backend server a list of one or more applications for which the user has permission to access, that are relevant to the current EHR session, or the like. In some exemplary embodiments, the EHR adapter may load the listed applications in one or more respective iframes that may be dynamically injected to the page by the extension, e.g., in response to an instruction from the EHR adapter, in response to an instruction from the backend server, or the like. Alternatively, the extending applications may be loaded in any other widget, GUI element, structure, or the like. In some exemplary embodiments, the iframes may not have access to the DOM of the EHR page, and may therefor rely on the EHR adapter to identify events of interest. In some exemplary embodiments, instead of accessing the DOM, the iframes may obtain page properties and events via the extension, which may provide indications of such events to the EHR adapter. In some exemplary embodiments, the EHR adapter may enable to load the iframes with respective resources, and may enable to add, modify or remove iframes.

In some cases, an injected iframe may load an extending application by embedding a document, e.g., a HyperText Markup Language (HTML) document associated with the storage of the extending service within the browsed page of the currently used EHR system, by embedding a GUI element therein, by embedding executable code therein, or by comprising any other resource. In some exemplary embodiments, the iframe may provide an extending application by executing a Uniform Resource Locator (URL) link embedded in the iframe, or any other link that is associated to the iframe, embedded therein, pointed by the iframe, or the like.

In some exemplary embodiments, an iframe may load itself with extending applications from the platform of the extending service, or from any other server, such as by executing a linked URL that is linked to an extending application, thereby loading the extending application over the EHR system and presenting the user with augmented data and functionality. In some exemplary embodiments, an iframe that is injected in the page may be enabled to communicate with both the backend of the extending service, and executing infrastructure such as the EHR adapter. For example, an iframe may communicate with the EHR adapter using inter-browser communications such as postMessage communications, and the iframe may communicate with the storage using Hypertext Transfer Protocol (HTTP) communications.

In some exemplary embodiments, the extension may be configured to inform iframes loading extending applications about occurring page events via runtime infrastructure. In some exemplary embodiments, the extension may be configured to update or inform the EHR adapter about the occurring events, and the EHR adapter may be configured to convert or translate event data to a cross-EHR and cross-application format, e.g., which may correspond to a format used by the applications. In some exemplary embodiments, as each EHR system may retain, in its backend server, data records in various uncorrelated formats, code languages, variable names, or the like, the EHR adapter may be configured to translate or convert a format of a specific EHR system to a cross-EHR format including a single representation of ongoing events and data that may be used for all of the extending applications. Determining a cross-EHR representation may be performed manually, such as by manually providing or obtaining a different conversion implementations for each EHR adapter, or automatically, such as by using computer vision techniques, automatic classifiers, data science modules configured to inspect the content of the page, text recognition methods, image recognition methods, monitoring network traffic, using Windows™ API calls or any other API calls, performing dynamic injection of DLLs, or the like, to obtain data in different versions and convert the data to the cross-EHR version. The conversion may be performed by the EHR adapter for one or more EHR systems, such as for EHR systems of certain clinics, payers, providers, covered entities, or the like. In some exemplary embodiments, each type of EHR system may be allocated an EHR adapter that is enabled to convert or translate the data from the EHR systems to a unified cross-EHR format. In some cases, the cross-EHR format may be generated to comprise a non-sensitive form, such as a form that does not comprise PHI information, Personally Identifiable Information (PID information, or the like. For example, the EHR adapter may convert event data to a common event pattern or description that does not include the name of the patient, an identifier of the patient, a timestamp of the event, or the like. In other cases, the cross-EHR format may comprise a sensitive form, which may comprise PHI information, PII information, or the like, in a unified cross-EHR format. In some exemplary embodiments, the EHR adapter may provide the cross-EHR version of the events to the runtime infrastructure, which may be configured to inform the extending applications loaded in the iframes of the events.

In some exemplary embodiments, the runtime infrastructure may be utilized to dynamically load code, e.g., of one or more extending applications, over the EHR system, such as by loading the iframes with respective URLs. In some exemplary embodiments, the runtime infrastructure may enable to adjust the extending applications that are loaded in the iframes by adding, modifying or removing URLs from the iframes, and reloading the iframes. In some exemplary embodiments, the runtime infrastructure may dynamically adjust or modify one or more extending applications that are loaded in iframes, such as by modifying their URLs and reloading the iframes, modifying their link to resources and reloading the iframes, modifying a code of the resources to which a URL points, modifying resources to which a URL points, or the like. For example, the user may wish to book a physician office visit with a provider that is supported by her payer. However, the EHR system that is used by the user may provide a list of physicians according to the alphabetical order, which may not indicate which physicians are more recommended, have better results, are cheaper, are available in relevant times, or the like. In such a case, the runtime infrastructure may load an extending application over an iframe, or activate the extending application, in order to provide an augmented list that are listed according to a desired rating, e.g., a list of physicians that are supported by the user's payer, physicians listed according to ratings from multiple users, physicians listed according to historic lengths of the overall treatment, physicians listed according to historic results, physicians listed according to historic treatments analysis, physicians listed according to a rating determined by the extending service, the diagnosis of the patient, the desired procedures, the specialty of the physicians, a distance of the physicians from the patient's home, a distance of the physicians from the patient's work, or the like. For example, the historic treatments analysis may indicate that a provider that is declared as orthopedist has historically performed dozens of knee surgeries, thereby indicating that she can be listed as a knee specialist. In some cases, in case the extending application may not have an available iframe on which it can be loaded, the runtime infrastructure may instruct the extension to inject an iframe into the page, and then load the extending application therein.

In some exemplary embodiments, the functionality of the extending applications may change dynamically, during the execution time of the extending application, without requiring modifying in any way the extension or the runtime infrastructure, thus complying with one or more privacy regulations such as GOOGLE™ restrictions. In some exemplary embodiments, while iframes may be dynamically loaded in runtime, the extension may remain constant, with a constant code, structure, SDK, or the like, without being dynamically loaded. In some exemplary embodiments, iframes may be adjusted by the runtime infrastructure to point to a different application. For example, an extending application may be loaded in an iframe, and adjusted to point to a new application or application version in runtime, such as in response to real time events that are monitored by the extension, after which the new application or version may be reloaded and executed in the iframe instead of the previous application. According to this example, new versions and applications are re-loaded without requiring any installation or modification of assets or code at a client side. In some cases, the runtime infrastructure, the EHR adapter, or the like, may be loaded in respective visible or invisible iframes, and adjusted in runtime, such as in response to real time events that are monitored by the extension.

Another technical solution provided by the disclosed subject matter is providing a platform for cross-entity applications. In some exemplary embodiments, a platform comprising the extension, the runtime infrastructure, the EHR adapter, and the extending service may be utilized to enable multiple entities or vendors that may or may not be authorized to handle PHI data of patients to generate or create extending applications for EHR systems. For example, the disclosed platform may be used as a marketplace of extending applications, enabling users to obtain or install extending applications that they desire for their EHR systems, without compromising on their privacy. According to this example, the marketplace may comprise only client-side applications that are available in the marketplace, which may be handled by the disclosed platform without enabling the applications to replace portions of the platform.

In some exemplary embodiments, unauthorized extending applications from unauthorized entities may not be enabled to communicate directly with the backend of the extending service, as its storage may comprise sensitive data. Alternatively, the unauthorized extending applications may be enabled to communicate directly with the backend of the extending service, but the extending service may identify that the applications are unauthorized and avoid from providing sensitive data thereto. In some exemplary embodiments, the unauthorized extending applications may interface and interact only with the runtime infrastructure, which may indicate thereto a cross-EHR cross-application events in a non-sensitive version, in case the applications are registered thereto, and obtain therefrom a responsive action or instruction. In some exemplary embodiments, the platform may control any data that is provided to applications and implementation of responsive actions.

In some exemplary embodiments, since the EHR adapter may convert real time EHR events to cross-EHR events, which may be forwarded to the runtime infrastructure and indicated only to registered applications that are registered to such events, the unauthorized third party server of the unauthorized application may not have access to sensitive event data of the user. Instead, the unauthorized provider or server may merely be enabled to provide an application that can generate a responsive command or action in response to certain cross-EHR events, without necessarily obtaining at the server an indication that the event occurred, that a response to the event was instructed, or without having any indications of event properties beyond the mere occurrence of the event.

In some exemplary embodiments, the cross-EHR representation of events may create an abstraction layer over EHR APIs, e.g., in order to prevent the third party applications from accessing the EHR systems, as they may be exposed to cross-EHR events and data only. In some exemplary embodiments, the abstraction layer may enable the various entities to write and generate custom business logic for a cross-EHR application that is configured to use the abstraction layer without being aware of the EHR vendor, without communicating therewith, or the like. In some exemplary embodiments, any third party entity or vendor may be enabled to register or provide extending applications to the platform, without exposing the EHR internals to the third party entity, and without requiring the vendor to specify the code of the application to properties of a specific EHR system.

In some exemplary embodiments, the architecture of the platform may contain an agent such as the browser extension, a computer vision based agent, a digital signal extraction agent, or the like, which may be responsible for low level interactions with the EHR system, e.g., monitoring EHR events and data. In some cases, in addition to or instead of the browser extension, such as in the case of an EHR system that comprises a desktop EHR system that is not rendered by a browser, the agent may comprise one or more alternative agents such as a computer vision based agent, a digital signal extraction agent, a Windows™ API (WinAPI) agent, a sniffer, or the like. In some exemplary embodiments, the agent may comprise a computer vision-based agent that may be enabled to monitor and identify events of the EHR system using one or more computer vision techniques, classifiers, identifiers, or the like. In some exemplary embodiments, computer vision techniques may enable to extract and identify content, and EHR events such as cursor activities, keyboard activities, or the like, from a displayed screen of an end device. In some exemplary embodiments, the agent may comprise a digital signal extraction agent comprising a binary that may be linked or injected into the EHR code, enabling to monitor the activity of the EHR system in runtime. In some exemplary embodiments, the agent may comprise a sniffer that may be utilized to monitor events issued by the EHR code. In some exemplary embodiments, the agent may comprise a reverse engineering module that may be utilized to monitor events using one or more reverse engineering techniques. In some exemplary embodiments, the agent may comprise a virtual machine that runs the EHR code and may be utilized to monitor events. Alternatively, EHR events may be monitored using an accessibility toolkit of the underlying Operating System (OS), e.g., using an OS provided screen reader, an OS provided event identifier, or the like.

In some exemplary embodiments, the architecture of the platform may contain EHR adapters for respective EHR systems, which may correspond to the runtime infrastructure. In some exemplary embodiments, the EHR adapters may communicate with the agent, obtain events therefrom, convert them to a cross-EHR form, and provide them to registered applications. In some exemplary embodiments, an EHR adapter for a specific EHR system may be responsible for monitoring or processing events of the EHR system that are obtained from the agent's API, and converting the events into a cross-EHR structure or format. In some exemplary embodiments, the EHR adapter may be embedded in the DOM of the EHR page, e.g., in an iframe, but may not be visible from a UI perspective, in contrast to cross-entity applications loaded in iframes that in some cases may be visible as part of the UI, the DOM, or the like.

The EHR adapter may be loosely coupled with a DOM of a specific EHR system, as, in order to enable conversion of event formats from an EHR system to cross-EHR representations, an adapter may be configured to match a format of a specific DOM of an EHR system. In some exemplary embodiments, an EHR-specific event or instruction may refer to an instruction that is represented in a manner that matches the syntax, format, form, language, API calls, code mapping, or the like, of a specific EHR system, and not necessarily to other EHR systems. In some exemplary embodiments, a cross-EHR instruction or event may refer to an instruction that is represented in the same manner for all or multiple EHR systems, and at all or multiple extending applications. A same cross-EHR representation of events, instructions, or the like, may be used by multiple applications for multiple EHR systems. In some exemplary embodiments, registered extending applications may be configured to communicate with the runtime infrastructure of the disclosed platform using a cross-EHR form of events. In some cases, a same adapter may be used for two or more EHR systems, e.g., similar EHR systems with different owners.

In some exemplary embodiments, the runtime infrastructure may indicate events to registered applications using a cross-EHR form of the events. In some exemplary embodiments, upon obtaining an indication of a registered event, registered applications may respond with cross-EHR instructions, which may be converted to an EHR-specific form by the runtime infrastructure. In some exemplary embodiments, the runtime infrastructure may convert the commands to the EHR-specific or clinic-specific API calls, which may be implemented by an agent such as the browser extension. For example, an instruction from an application may comprise a general form of an API call, and the runtime infrastructure may convert the instruction to an EHR-specific API call that matches the underlying EHR system. As another example, an instruction from an application may comprise a general form of a code, and the runtime infrastructure may convert the instruction to an EHR-specific code that matches the underlying EHR system and can be executed by the agent over the EHR system. Additionally or alternatively, the runtime infrastructure may invoke an automated process for extracting requested information without the use of an API, such as using computer vision techniques, using a sniffer process, scraping information from the memory, or the like.

One technical effect of utilizing the disclosed subject matter is creating a smooth and seamless integration of an extending application with the underlying EHR system, without having access to source code of the EHR system, while enabling the extending application to push valuable content to a user's workflow in an intuitive seamless manner. In some exemplary embodiments, based on a backend storage integrating multiple data sources that are associated with the patient, an extending application may be enabled to provide additional useful data, functionalities, or the like, that are not offered by the underlying EHR system. Utilizing the extending service may enable to eliminate challenges of ingesting, processing, storing, and utilizing healthcare data, by providing an extending application that is loaded over the workflow and provides missing or additional data, functionality, or the like. The extending application may be executed over multiple EHRs, payer systems, provider systems, or the like.

Another technical effect of utilizing the disclosed subject matter is enabling to utilize patient records and related data from various separated systems, e.g., EHR MW Ref GLAP 11969A GA Ref 752-1.1 systems, to generate extending applications which may enable the patient or a caretaker of the patient to locate treatments gaps of the patient, to diagnose the patient in a more informed or accurate manner, to inform the patient with provider options that are made available to her by her payer, to inform the patient of additional information regarding the provider options, or the like.

Yet another technical effect of utilizing the disclosed subject matter is creating a constant API on top of the EHR system, which may enable extending applications to access, modify, and receive updates from the EHR system and act thereon. In some exemplary embodiments, this architecture enables dynamic functionality improvements over EHR systems, without exposing the EHR system to the risks of dynamic code updates, and with a minimum footprint on the underlying EHR systems. In some exemplary embodiments, utilizing the extension enables dynamic functionality improvements.

Yet another technical effect of utilizing the disclosed subject matter is enabling an extending service to dynamically load extending applications over a web-based EHR system, a desktop-based EHR system, or any other iframe-supporting system without deployment of the extending service on the edge station, such as by using a browser extension that can be used for adding new functionalities in real time, for adjusting functionalities in real time, or the like, without requiring to update a version of the extension per new functionality. In some exemplary embodiments, in some cases, the agent may require edge station installation, such as in order to install a browser extension, a Windows™ agent, or the like.

Yet another technical effect of utilizing the disclosed subject matter is enabling extending applications to access, modify, and receive updates from various EHR systems including web-based EHR systems, EHR websites, desktop-based EHR systems, or the like. The agent may comprise a browser extension in the case of EHR websites, or a desktop agent in the case of desktop-based EHR systems that are retained at the end device such as at the desktop thereof.

Yet another technical effect of utilizing the disclosed subject matter is providing a platform that enables entities to generate a single application for multiple EHR systems, without having access to unauthorized data. In some exemplary embodiments, the EHR adapter of the platform may convert the EHR events to a standard representations in each EHR system for which the adapter is configured, without the application provider being required to perform any adaptations or adjustments to specific EHR systems. Using the API of the EHR may enable various application providers to provide a multi EHR application to their clients, that do not have access to the storage of the extending service. In some exemplary embodiments, having a single application for multiple EHR systems, instead of utilizing a different application for each EHR system, may save developing time, memory storage, execution time, or the like.

The disclosed subject matter may provide for one or more technical improvements over any pre-existing technique and any technique that has previously become routine or conventional in the art. Additional technical problem, solution and effects may be apparent to a person of ordinary skill in the art in view of the present disclosure.

Referring now to FIG. 1 illustrating a flowchart diagram of a method, in accordance with some exemplary embodiments of the disclosed subject matter.

In some exemplary embodiments, a software agent may be configured to monitor for one or more events in an underlying EHR system. In some exemplary embodiments, the software agent may be configured to monitor and interact with a DOM of a page of an underlying EHR system. In some exemplary embodiments, the software agent may comprise a browser extension that may be executed by a browser. In such a case, the browser may be configured to render the page of the EHR system. In some exemplary embodiments, the software agent may comprise a desktop agent, and the EHR system may comprise a desktop-based EHR system that is not executed in a browser. In such a case, the desktop agent may be configured to be executed over the desktop-based EHR system.

In some exemplary embodiments, in case the agent comprises a browser extension, the browser extension may be composed of a one or more portions, scripts of the like, such as a background script and a content script. In some exemplary embodiments, the background script may enable the extension to interaction with the API of the browser such as for storage purposes, in order to open a new tab of the browser, in order to send a request to a third party such as a backend of the extending service, with a database of the extending service, or the like. In some exemplary embodiments, the background script may not have access to the DOM of the browsed page. In some exemplary embodiments, the content script may enable the extension to access the DOM of the EHR website, the EHR web application, the EHR desktop application, or the like. In some exemplary embodiments, as the content script may have access to the DOM of the browsed page, the content script may handle the interface of the user such as by modifying the interface, injecting iframes into the interface, accumulating data therefrom, or the like.

In some exemplary embodiments, the following steps may be performed in order to implement one or more augmented functionalities that are not provided by an underlying EHR system.

On Step 110, the software agent may load, dynamically, a runtime infrastructure in a first iframe that may be embedded in the page of the EHR system. In some exemplary embodiments, the agent may load an EHR-specific EHR adapter that may be specifically designed or tailored based on the EHR system, e.g., to match the syntax, format or structure of the EHR system, over the page. In some exemplary embodiments, the runtime infrastructure may lack a GUI representation, such as by comprising an invisible iframe that does not embed a visible resource such as a visible GUI element, a visible document, or the like, which may not be perceivable in a display of a user device. Alternatively, the runtime infrastructure may comprise a visible GUI.

In some exemplary embodiments, the software agent may be configured to inject the first iframe in the page of the EHR system and cause the runtime infrastructure to be loaded into the first iframe. In some exemplary embodiments, the software agent may inject the first iframe into the page or the DOM of the EHR system, e.g., upon obtaining runtime infrastructure that matches the specific EHR system that is being used from the backend of the extending service, upon obtaining a list of relevant extending applications from the backend, or the like.

On Step 120, the runtime infrastructure may be configured to load, dynamically, one or more extending applications in respective second iframes that may be embedded in the page of the EHR system. In some exemplary embodiments, the software agent may be configured to inject the second iframes in the page of the EHR system and enable the runtime infrastructure to load an extending application into a second iframe. In some exemplary embodiments, the runtime infrastructure may be configured to dynamically load the extending application in the second iframe by provisioning a URL of the extending application to be loaded in the second iframe. In some exemplary embodiments, the URL may point to a code of the extending application, a source thereof, or the like.

In some exemplary embodiments, the list of applications to be loaded may be available in a marketplace, which may enable any provider to upload a new application to the marketplace, and may enable any user to install any desired application from the marketplace. In some exemplary embodiments, the runtime infrastructure may be configured to retrieve from a server of the extending service a list of extending applications to be loaded in the page, e.g., extending applications that are of interest to the user (e.g., were installed by the user, match the context of the page, or the like) and the user has permission to access their functionality in the current context of the page. In some exemplary embodiments, the list of applications to be loaded may be determined based on access permissions of a user of the EHR system to applications in an application repository, e.g., in a backend of the extending service.

In some exemplary embodiments, the list of applications to be loaded may comprise a first extending application that is loaded within the second iframe and a second extending application that is loaded within a third iframe, each belonging to a different organization associated with a different server. For example, the first extending application may be obtained from a first server that belongs to a first organization, client, EHR system, payer, provider, partner, or the like, and the second extending application may be obtained from a second server that belongs to a second organization, client, EHR system, payer, provider, partner, or the like. In some exemplary embodiments, the runtime infrastructure may be configured to dynamically load the second application in response to an event monitored by the agent, or based on any other calculation or identification. In some exemplary embodiments, the runtime infrastructure may be configured to dynamically load the second application within an existing iframe, within a new iframe, or the like. In some exemplary embodiments, the runtime infrastructure may be configured to dynamically load the second application in an additional, e.g., third, iframe embedded in the page, such as by provisioning a URL to be loaded in the third iframe. In some exemplary embodiments, the third iframe may be injected in the page by the software agent, e.g., prior to or after identifying the event, and the URL may point to a code of the second application, such that any modification of the code may affect the execution of the URL in the third iframe. In some exemplary embodiments, the runtime infrastructure may be configured to dynamically load the second application in an existing iframe, e.g., the second iframe, which may be occupied with a different URL. The second application may be loaded into the second iframe by provisioning a URL of the second application to be loaded in the second iframe, thereby changing the URL of the first application with a URL of the second application within the same iframe. In some exemplary embodiments, the URL of the second application may be configured to point to a code of the second application, thereby replacing or adjusting a URL of the first application and enabling to dynamically load the second application in the second iframe. In some cases, the second application may comprise an updated version of the first application, a separate application from a different vendor, or the like.

In some exemplary embodiments, an extending application may comprise a GUI component that may be visible, e.g., including a visible resource, a visible UI widget, a visible embedded document, or the like. In some exemplary embodiments, an extending application may comprise a resource or code that is not visible, has no GUI component, or the like, e.g., an automation process. In some exemplary embodiments, the extending applications may each retain business logic that may be configured to manipulate the GUI component, perform a data presentation, load resources over the EHR page, or the like, in order to enable an additional functionality to be loaded over the page.

In some exemplary embodiments, an extending application may comprise an augmented or added functionality that is configured to be loaded in a respective iframe embedded in the page. In some exemplary embodiments, the functionality may be absent in the page of the EHR system, absent in the EHR system, may not be served by the EHR interface, or the like. In some exemplary embodiments, the functionality may be determined to be absent from the EHR system, e.g., by the runtime infrastructure, an EHR adapter, the software agent, or the like. For example, an extending application may be configured to load a resource that is associated with a user of an end device executing the software agent, that can be augmented to the workflow of the user, or the like. As another example, the extending application may comprise manipulating a GUI element such as a button associated with the extending service.

In some cases, the extending application may comprise an automation process or code that may be executed in an iframe loading the extending application, e.g., an invisible iframe lacking a GUI representation. In some exemplary embodiments, the automation process may not comprise a visual resource but rather an automation process that can be executed in the iframe and cause other portions of the GUI to be modified. In some exemplary embodiments, the automation code may be activated remotely such as by a remote server of an extending service, or locally such as by the software agent. For example, an automation process may be configured to imitate a user interaction with the user interface of the EHR system. As another example, the automation code may be configured to load from the backend server of the extending service a list of providers that match the user, which may be loaded by executing the code of the automation process.

On Step 130, the software agent may be configured to communicate events and responsive actions with the EHR adapter. In some exemplary embodiments, the agent may be configured to provide one or more first EHR-specific data, events, instructions, or the like, such as regarding identified events, to the EHR adapter. In some exemplary embodiments, the agent may be configured to provide the EHR-specific data in response to an instruction of the EHR adapter. For example, the EHR adapter may instruct the agent to monitor a component or element of interest. In some exemplary embodiments, the EHR adapter may be configured to receive the first EHR-specific data from the software agent, and translate the first EHR-specific data to first cross-EHR data or instructions, which may not be EHR-specific in their syntax, format, or the like, but rather may be used for any application in any EHR system. In some exemplary embodiments, the EHR adapter may communicate the first cross-EHR data to the runtime infrastructure, which may communicate the first cross-EHR data to extending applications that are registered to the event.

In some exemplary embodiments, the extending applications may be configured to instruct the EHR adapter to perform responsive actions in response to the monitored events, such as to augment data, load content, load resources, load applications, execute functions, modify GUI elements, or the like, over the page of the EHR system. In some exemplary embodiments, the EHR adapter may be configured to receive second cross-EHR instructions from the extending applications, such as regarding a responsive action to an event, and translate the second cross-EHR instructions to second EHR-specific instructions, which may be EHR-specific in their syntax, format, or the like. In some exemplary embodiments, the EHR adapter may communicate the second EHR-specific instructions to the software agent, such as in a form that specifically matches the underlying EHR system.

In some exemplary embodiments, the software agent may identify or monitor an event in the EHR system. For example, the event may comprise identifying a user-initiated search of a provider in the EHR system. In some exemplary embodiments, the software agent may notify the EHR adapter of the event, such as via an EHR-specific instruction that matches the underlying EHR system. In some exemplary embodiments, prior to notifying the EHR adapter of the event, the software agent may determine whether the event corresponds to a defined list of events, e.g., a whitelist of events, events that are permitted to be forwarded to the EHR adapter, events that are relevant to the EHR system, or the like. In some exemplary embodiments, in case the event corresponds to the defined list of events, the software agent may provide an indication of the event to the EHR adapter.

Figure 2:
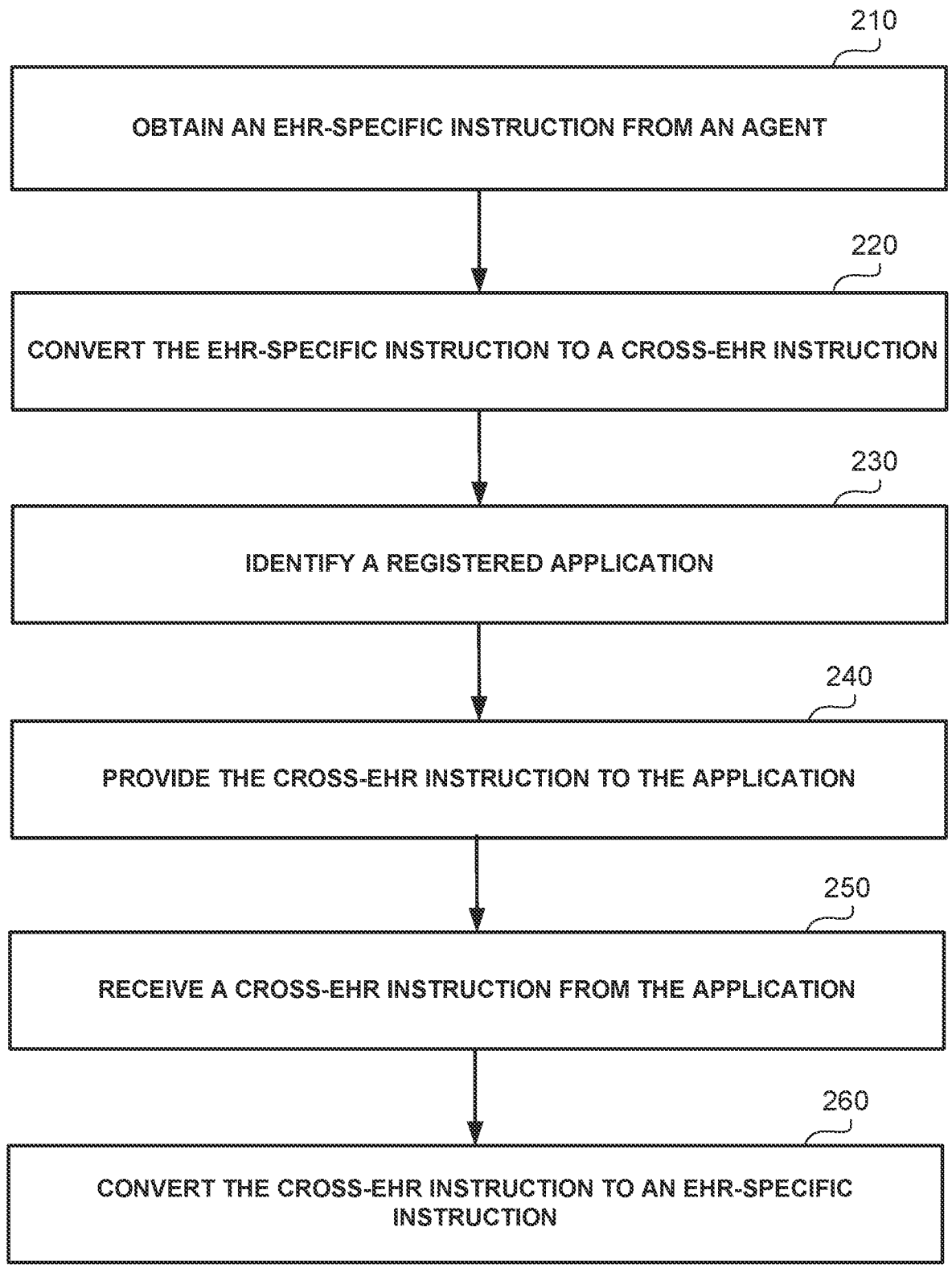
FIG. 2 illustrates a flowchart diagram of a method, in accordance with some exemplary embodiments of the disclosed subject matter.

In some exemplary embodiments, in response to the event indication, the EHR adapter may communicate with registered applications, e.g., according to the steps of FIG. 2. In some exemplary embodiments, the EHR adapter may obtain from the registered applications an indication of a responsive action such as a UI manipulation, a data update in the page of the EHR system, an automation of a sequence of interactions with the UI, processing of data from the page, or any other functionality that is to be performed in the page of the EHR system. For example, a responsive action may comprise an RPA that is configured to implement a sequence of interactions with the UI, such as a sequence of clicks on UI elements. In some cases, such as in case of a desktop agent, the EHR adapter may obtain from the registered applications indications of one or more additional responsive actions such as copying text to a clipboard and providing a pasted version of the text to the backend of the EHR system, or the like.

In some exemplary embodiments, the EHR adapter may provide to the software agent an EHR-specific instruction to perform the responsive actions. In some exemplary embodiments, the EHR-specific instruction may be configured to enable the agent to perform a UI manipulation in the page of the EHR system, a data update in the page of the EHR system, an API call, or the like, according to the instruction of the respective extending application.

In some exemplary embodiments, the software agent may execute the one or more responsive actions over the page, such as by modifying the DOM of the page and loading the resource within iframes embedded in the page, performing an automation process with the user interface of the page, or the like. In some exemplary embodiments, loading the resource over the page may provide the user with an augmented functionality that is not available at the EHR system. In some exemplary embodiments, the responsive action may be implemented as a manipulation of a GUI element in an iframe, an overlay presented over the browsed page, as an injected code that is embedded in the page, as an activation of a code that is embedded in an iframe, or the like. In some exemplary embodiments, the loaded resources may be adapted to the EHR interface and combined or embedded therewith.

In some exemplary embodiments, the runtime infrastructure may be enabled to load new code and provision new functionality in real time, such as by changing the URL, changing a backend of a resource to which the URL points, loading a URL over a newly injected iframe, or the like, without changing or modifying the software agent or the runtime infrastructure. In some exemplary embodiments, applications loaded in iframes may be adjusted or switched in real time by changing a URL or resource link of an iframe with another link of an application from the retrieved list of applications, and reloading the resources. In some exemplary embodiments, applications loaded in iframes may be adjusted or switched in real time by changing a resource to which the URL points, a backend to which the URL points, or the like, e.g., with an updated version of the resource, without changing the URL itself. In some exemplary embodiments, by enabling changes through authorized applications from the retrieved list of applications only, dangers imposed by a dynamic execution of a string representing client-side code may be prevented.

For example, after the first event, the agent may monitor the DOM of the page to identify a second event, indicate the second event to the runtime infrastructure, and, in response to the second event, obtain an instruction from the runtime infrastructure to adjust an iframe embedding the extending application to point to a second extending application, such as by changing a URL of the iframe. Alternatively, in response to the second event, the runtime infrastructure may instruct the agent to inject a new iframe in the page, and load a second application in the new iframe. In some exemplary embodiments, the runtime infrastructure may comprise a software component for enabling to instruct the agent to add on the fly new iframe elements, and to load therein resources such as information from the extending service, from a third party, or the like. In some exemplary embodiments, the runtime infrastructure may instruct the agent to insert additional iframes in the DOM of the page in response to an event, a determination, an automation execution, or the like. In some exemplary embodiments, the runtime infrastructure may modify and load extending applications over embedded iframes in EHR systems.

Referring now to FIG. 2 illustrating a flowchart diagram of a method, in accordance with some exemplary embodiments of the disclosed subject matter.

On Step 210, an EHR-specific instruction, data, event indication, or the like, may be obtained, at an EHR adapter, from a software agent e.g., in response to an indication of the EHR adapter indicating events of interest, GUI elements of interest, DOM elements of interest, or the like, to the agent. In some exemplary embodiments, upon receiving the indication, the agent may monitor the elements of interest and identify real time events associated thereto such as events involving the elements of interest, interactions therewith, or the like. In some exemplary embodiments, in response to detecting an event of interest, the agent may generate an EHR-specific instruction indicating the event of interest. In some exemplary embodiments, the EHR-specific event may correspond to the instructions of the EHR adapter that were provided to the agent. In some exemplary embodiments, the EHR-specific instruction may comprise an indication of an event that occurred in a DOM of a page of the EHR system, such as in real time. In some exemplary embodiments, the EHR-specific event or instruction may be obtained in a form that corresponds to the API of the underlying EHR system, to its DOM layout, or the like.

On Step 220, the EHR-specific instruction may be converted to a cross-EHR instruction at the EHR adapter. In some exemplary embodiments, the EHR adapter may translate or convert the EHR-specific instruction indicating the event to a cross-EHR instruction that can be provided to the runtime infrastructure, and from there to an extending application. In some exemplary embodiments, the cross-EHR instruction may comprise a general representation of the event, which can be used to describe events from multiple different EHR systems to multiple extending applications through a single runtime infrastructure, or the like. For example, the general representation may comprise a representation that corresponds to a format, syntax or language that is used by the extending applications.

In some exemplary embodiments, the EHR adapter may be configured to convert the event to a cross-application cross-EHR form, that can be provided and processed by any extending application. Accordingly, the respective extending applications may not be privy to the EHR-specific events, instructions, or the like, and may not have access thereto. In some exemplary embodiments, the EHR-specific events, instructions, or the like, in their EHR-specific form, may not be shared with the extending applications.

On Step 230, the EHR adapter may forward the cross-EHR instruction to the runtime infrastructure, which may identify a registered extending application. In some exemplary embodiments, the runtime infrastructure may determine that an application is registered to the cross-EHR representation of the event, e.g., based on application registration to cross-EHR cross-application events.

On Step 240, the cross-EHR instruction may be provided to the registered application, e.g., indicating the event thereto. In some exemplary embodiments, the runtime infrastructure may be configured to provide a cross-EHR indication of the event to registered applications that are registered to the event, as identified at Step 230. In some exemplary embodiments, the extending applications may be configured to utilize cross-EHR cross-application formats of events, instructions, or the like only, and may not be configured to handle EHR-specific instructions or event indications.

In some exemplary embodiments, upon obtaining a cross-EHR instruction, event indication, or the like, an extending application may execute a cross-EHR business logic, e.g., in order to determine a cross-EHR response to the event. In some exemplary embodiments, the extending applications may each retain business logic that may be configured to determine a responsive action for an identified event, such as a manipulation of a GUI component, an update of data, sending an API call, or the like.

On Step 250, a cross-EHR instruction may be received from the application, e.g., at the runtime infrastructure. In some exemplary embodiments, the cross-EHR response may be provided from registered applications to the runtime infrastructure. In some exemplary embodiments, the cross-EHR instruction may comprise a cross-EHR representation of a responsive action from the application, that is intended to be implemented in response to the event. In some exemplary embodiments, the responsive action may be configured to perform a UI manipulation in the page of the EHR system, to load a resource such as a GUI element, to present data, to perform a data update in the page of the EHR system, or the like, in response to the event.

On Step 260, the cross-EHR instruction may be provided from the runtime infrastructure to the EHR adapter, so that the EHR adapter can convert the cross-EHR instruction to an EHR-specific instruction. In some exemplary embodiments, the EHR adapter may translate or convert the cross-EHR instruction to an EHR-specific instruction that can be implemented directly by the software agent over the EHR system.

In some exemplary embodiments, the runtime infrastructure may be configured to communicate with extending applications using cross-EHR cross-application instructions, indications, or the like, that were converted by the EHR adapter or provided by the extending applications. In some exemplary embodiments, the EHR-based instruction may be provided to the agent in a form that can be executed over the specific EHR system, such as using a conversion to the specific EHR by the EHR adapter. Accordingly, the respective extending applications may not be privy to the EHR-based instructions obtained by the agent, and may not have access thereto.

In some exemplary embodiments, due to the conversions performed by the EHR adapter between EHR-specific formats and cross-EHR formats, the software agent may be enabled to communicate indirectly with the extending applications, in order to indicate thereto events and obtain therefrom responsive actions, e.g., via the runtime infrastructure.

Figure 3:
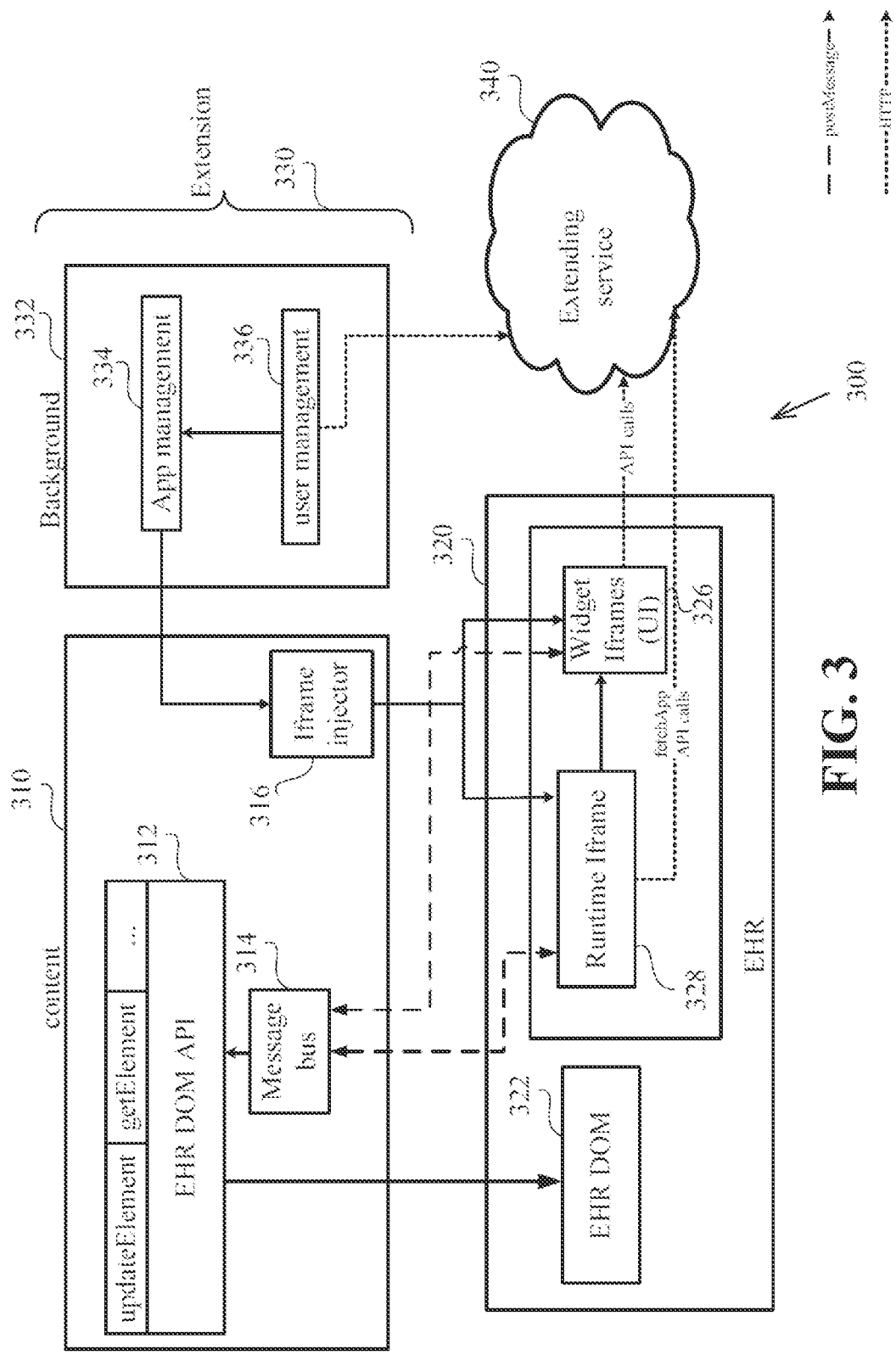
FIG. 3 shows a schematic illustration of an exemplary environment and architecture in which the disclosed subject matter may be utilized, in accordance with some exemplary embodiments of the disclosed subject matter.

Referring now to FIG. 3 showing a schematic illustration of an exemplary environment, in accordance with some exemplary embodiments of the disclosed subject matter.

In some exemplary embodiments, Environment 300 may comprise a software agent such as an Extension 330 of a browser containing separate portions, scripts, or the like, e.g., a Content 310, which may be configured to handle an access to the EHR interface, and a Background 332, which may be configured to communicate with the backend of the extending service, such as via a rendering browser. In some exemplary embodiments, Environment 300 may comprise an EHR System 320, which may not be associated with the Extension 330 or with the extending service providing the Extension 330. EHR System 320 may comprise an EHR DOM 322, containing the DOM representation of the EHR pages. In some exemplary embodiments, Environment 300 may comprise an Extending Service 340, which may be configured to provide extending applications that can be executed over EHR systems, as well as EHR adapters for underlying EHR systems such as EHR System 320.

In some exemplary embodiments, Extension 330 may be configured to be executed by a browser that is rendering EHR System 320. In some exemplary embodiments, a Background 332 script of Extension 330 may comprise an Application Management 334 component and a User Management 336 component, and may enable Background 332 to communicate with the browser such as in order to reach Extending Service 340 via the browser and obtain therefrom a list of applications.

In some exemplary embodiments, a Content 310 script of Extension 330 may comprise an EHR DOM API 312 component, which may enable Content 310 to monitor and modify the user interface or EHR DOM 322 of EHR System 320, such as by using hooks, API calls, or any other monitoring technique that can be used by a browser extension. In some exemplary embodiments, EHR DOM API 312 may contain a thin API layer which may access the DOM of the EHR application, e.g., EHR DOM 322 of EHR System 320, monitor EHR DOM 322 with any monitoring technique of browser extensions, scrape the EHR DOM 322, or the like. In some exemplary embodiments, Content 310 may also comprise an Iframe Injector 316 enabling to inject Widget Iframes 326 and a Runtime Iframe 328 to EHR DOM 322. Runtime Iframe 328 may comprise an iframe over which an EHR adapter or runtime infrastructure may be executed, and may or may not be visible. Widget Iframes 326 may comprise iframe over which extending applications may be loaded. Content 310 may comprise a Message Bus 314 enabling to exchange messages with the injected iframes.

In order to load an EHR adapter in Runtime Iframe 328, Content 310 may obtain the EHR adapter from Extending Service 340 such as via Background 332, which may provide it to Content 310, and enable Content 310 to load the adapter within Runtime Iframe 328. For example, Background 332 may send Extending Service 340 a request to obtain an adapter to EHR System 320, and in response, Background 332 may obtain the adapter. In order to load extending applications in Widget Iframes 326, Content 310 may obtain the applications from Extending Service 340 such as via Background 332, which may provide it to Content 310. In some exemplary embodiments, Background 332 may obtain from Extending Service 340 an adapter that is adapted to the specific EHR System 320, a list of applications that match EHR System 320 and are authorized for the user account, e.g., according to Application Management 334 which may pull its data from Extending Service 340, or the like. Background 332 may forward the data to Content 310. In some exemplary embodiments, Application Management 334 in Background 332 may be configured to determine a list of applications or data from the storage of Extending Service 340 or from any other location that can be loaded for the user, e.g., applications that are authorized for the user according to the user's workplace, membership, organization, identity, account, or the like, according to user categories or properties determined by User Management 336 (which may pull its data from Extending Service 340), or the like. In some exemplary embodiments, User Management 336 may determine permissions of a user account. For example, User Management 336 may indicate that the user only has permission to access data records that belong to the user, and data records that describe providers with which the user's payer works. In some exemplary embodiments, Application Management 334 may determine that a list of one or more extending applications can be loaded for a current user or user account, e.g., in accordance with the user's permissions determined by User Management 336, in accordance with a context of EHR System 320, in accordance with loaded configurations relating to the user, configurations relating to the user's organization, configurations relating to the user's installed applications, or the like. For example, the list of applications may comprise applications that the user has permission to access and are relevant to a browsed page. In some exemplary embodiments, Iframe Injector 316 may inject for the obtained applications respective Widget Iframes 326.

In some exemplary embodiments, Extension 330 may access the DOM of the EHR System 320, e.g., EHR DOM 322. Extension 330 is enabled to access EHR DOM 322 due to EHR DOM API 312 of Content 310, which provides for an API for accessing and potentially manipulating EHR DOM 322. In some exemplary embodiments, in order to enable the Extending Service 340 to provide an extending application in a secure and privacy-retaining manner, Extension 330 may verify the user's identity prior to loading Runtime Iframe 328, e.g., by scraping the user's EHR credentials and utilizing them for a sign in process of Extending Service 340, by utilizing a Single Sign-On (SSO) flow without scraping the user's EHR credentials, or in any other way.

In some exemplary embodiments, Iframe Injector 316 may load the EHR adapter in the Runtime Iframe 328 such as by embedding therein a URL that points to Extending Service 340 or any other EHR adapting source. In some exemplary embodiments, Runtime Iframe 328 may load the adapter from a platform of Extending Service 340, e.g., by executing the URL. In some exemplary embodiments, Runtime Iframe 328 may function as an adapter between Extension 330 and Widget Iframes 326, enabling Extension 330 to forward events to Widget Iframes 326 via a conversion or adaption of Runtime Iframe 328.

In some exemplary embodiments, Runtime Iframe 328 may be configured to communicate with both Extending Service 340 and Extension 330. Runtime Iframe 328 may communicate with Extending Service 340 by exchanging Hypertext Transfer Protocol (HTTP) API calls with a platform of Extending Service 340. In some exemplary embodiments, Runtime Iframe 328 may be configured to communicate with Extension using one or more communication protocols or methods such as a "postMessage" method, or any other communication method that may enable cross-origin communication between an iframe and a browser extension. For example, the postMessage method may enable Runtime Iframe 328 to communicate with Extension 330, via Message Bus 314 of Extension 330, via EHR DOM API 312, or the like. Iframes such as Widget Iframes 326 and a Runtime Iframe 328 may also communicate with each other using postMessage communications, or any other communication type. The messages of Runtime Iframe 328 with Extension 330 may comprise in-browser messages that may be wrapped in an Inter-Process Communication (IPC)-like interface. In some exemplary embodiments, using an IPC interface, iframes such as Runtime Iframe 328 may communicate with Extension 330, as part of the application abstraction. Background 332 may communicate with Extending Service 340 via HTTP messages. In some exemplary embodiments, Widget Iframes 326 may communicate HTTP-based API calls, or any other type of communications, with Extending Service 340. In some exemplary embodiments, Widget Iframes 326 may communicate with Message Bus 314, Runtime Iframe 328, or the like, using one or more communication protocols or methods such as a postMessage communication method.

In some exemplary embodiments, EHR DOM API 312 may monitor events in EHR System 320 and update Runtime Iframe 328 regarding events that occurred in the EHR DOM 322, e.g., in case they match a defined whitelist of events, do not match a blacklist of events, are defined as events of interest, or the like. Widget Iframes 326 may not have any access to the DOM of the page, e.g., EHR DOM 322. Therefore, in order to obtain information about the page events and data, Widget Iframes 326 may be informed about any page data or events via Runtime Iframe 328, which may be informed of such data from EHR DOM API 312 of the Content 310. In some exemplary embodiments, upon obtaining indications of events from Extension 330, which may be provided in an EHR-specific format, such as via Message Bus 314, Runtime Iframe 328 may notify the iframes of Widget Iframes 326 regarding the events. Runtime Iframe 328 may obtain DOM events that are monitored by EHR DOM API 312, and indicate the events to registered applications of Widget Iframes 326 that are registered to the events, to subscribed iframes, to all iframes, or the like, so that they can respond to the events in case such a response is configured to be provided.

In some exemplary embodiments, an EHR adapter to EHR System 320, which may be comprised in Runtime Iframe 328, may be configured to convert or translate EHR-specific data from Extension 330 to a cross-EHR format, with which the applications loaded in Widget Iframes 326 may communicate, process, execute, or the like. The cross-EHR format may comprise an abstraction layer of events that may be used by the applications, e.g., all the extending applications, a unified format thereof, or the like. In some exemplary embodiments, each EHR system such as EHR System 320 may retain data records in different formats, orders, syntax, protocols, or the like, thereby requiring an EHR adapter to mediate between the applications and each EHR System 320. Although Runtime Iframe 328 may match a vendor of a certain EHR system, such as EHR System 320, the events and protocols used by Runtime Iframe 328 may be identical for all EHR systems, enabling instances of Runtime Iframe 328 to handle multiple extending applications from various sources.

In some exemplary embodiments, the registered applications loaded in Widget Iframes 326 may obtain the cross-EHR data from Runtime Iframe 328, and execute business logic to determine a responsive action for the event. In some exemplary embodiments, Runtime Iframe 328 may obtain cross-EHR responses to events from the registered applications, and adapt the cross-EHR responses to EHR-specific API calls or other EHR-specific instructions that can be executed or implemented by Extension 330 over EHR System 320. Runtime Iframe 328 may provide the EHR-specific instructions to Message Bus 314 in a format that matches the underlying EHR system. In some exemplary embodiments, in response to obtaining the EHR-specific instructions from Message Bus 314, EHR DOM API 312 component in Content 310 may be configured to generate API calls such as calls to update an element in the DOM of the EHR system, calls to record an element from the DOM, send the API calls to EHR System 320, or the like. For example, EHR DOM API 312 may add one or more GUI elements to the DOM in response to instructions from Runtime Iframe 328. In case Runtime Iframe 328 determines that, in response to an event, an additional iframe is needed to load an additional application, a request may be made to Extension 330 to inject a new iframe, e.g., via Iframe Injector 316. Iframe Injector 316 may inject one or more iframes in EHR DOM 322, in response to the instructions, so that one or more additional applications could be executed therein.

In some exemplary embodiments, Runtime Iframe 328 may enable to dynamically modify or load extending applications over Widget Iframe 326. In some exemplary embodiments, Runtime Iframe 328 may obtain from Extending Service 340 a list of applications and load them above Widget Iframe 326 in EHR DOM 322, such as by embedding in each iframe an URL of the respective extending application. In some exemplary embodiments, upon determining that a new application should replace a current application running in an iframe, Runtime Iframe 328 may modify the iframe in real time by changing its URL and replacing it with a URL of the new application, adjusting parameters within the URL, removing the iframe and replacing it with a new iframe pointing to the new application, or the like. In some exemplary embodiments, the applications that are loaded in Widget Iframes 326 may be modified by inserting a different URL in the iframe, e.g., by Runtime Iframe 328, thereby causing the iframe to point to a different URL or resource. Widget Iframe 326 may load resources of an extending application from a platform of Extending Service 340, e.g., directly by executing the URL, via Runtime Iframe 328, or the like. For example, an application executing in Widget Iframe 326 may be configured to determine a responsive action to an event, such as including loading from Extending Service 340 a list of providers that are supported by the user's payer, in case EHR DOM API 312 indicates that the data is missing in EHR System 320. In some exemplary embodiments, the data may be adapted to the EHR interface of EHR System and combined or embedded therewith, e.g., by the application, Extension 330, or the like.

In some exemplary embodiments, an exemplary pseudo code for utilizing Environment 300 may comprise a configuration of the disclosed components, e.g., as follows:

```
/*
*
*Background
*
*/
const {applications, adapter}=getUser( ); // API call to extending server sendToContent('initMsg', applications, adapter);
/*
*
* Content
*
*/
const Events = {
   getAttribute: (params) => { },
   scrape: (params) => { },
   fetchData: (params) => { },
   reloadWindow: (params) => { },
   injectWidget: (params) => { },
   // . . .
};
// Create listener to events from Background
createBackgroundListener(message => {
   if (message === 'initMsg') {
      const runtimeFrame = createRuntimeIframe('runtime.get.com', adapter, applications);
      DOM.add(runtimeFrame);
   }
});
// Create message bus to events from iframe adapters
DOM. addEventListener('message', event => {
   if (event is in Events) {
      const response = event( ); //execute the event and get the response
      event. adapter. sendResponse(response);
   }
});
```

As described by the pseudo code, Background 332 may have access to communications with an executing browser, via which Background 332 may reach Extending Service 340 and communicate therewith. Background 332 may obtain from Extending Service 340 an EHR adapter for EHR System 320 to be loaded in Runtime Iframe 328, and a list of applications that are to be executed in Widget Iframe 326. Background 332 may forward the data regarding the EHR adapter and the list of applications to Content 310 via an initialization message.

In some exemplary embodiments, inside Content 310, an API such as EHR DOM API 312 component may be configured to exchange calls with a DOM of an EHR page, e.g., EHR DOM 322, enabling to obtain data from the DOM, instruct actions to occur in the DOM, add data to the DOM, or the like. Content 310 may have access to EHR DOM 322, from which Content 310 may identify events, obtain attribute parameters, scrape parameters, fetch data, or the like. Content 310 may be enabled to modify EHR DOM 322 such as by reloading a window, injecting an iframe, or the like. In some cases, actions performed by Content 310 or monitored by Content 310 may matched against a defined Events object, such as indicating events of interest.

In some exemplary embodiments, upon obtaining the initialization message from Background 332, Content 310 may identify the message as an initialization message of the user, and inject an initial listener such as Runtime Iframe 328 into EHR DOM 322, e.g., by Iframe Injector 316. Iframe Injector 316 may initialize Runtime Iframe 328 with a URL or link that is associated to the EHR adapter, enabling the EHR adapter to be loaded therein. In some cases, Iframe Injector 316 may inject one or more additional iframes such as Widget Iframes 326 for the extending applications, over which Runtime Iframe 328 may load the applications, e.g., as part of a loading process of the extending applications.

In some exemplary embodiments, Message Bus 314 may be created by Content 310 for facilitating communications of events between Content 310 and Runtime Iframe 328. In case Content 310 determines that an identified event matches the defined Events object, a defined whitelist, or the like, Message Bus 314 may notify Runtime Iframe 328 of the event. Runtime Iframe 328 may convert the EHR-specific event to a cross-EHR event, which may be provided to registered applications loading over Widget Iframes 326. In some exemplary embodiments, the extending applications may be configured to determine a response to the event, and indicate the respond to Runtime Iframe 328 as a cross-EHR instruction to implement an action over EHR System 320, e.g., to manipulate a GUI element presented by the respective iframe, to execute an automation code in the iframe, or the like. Runtime Iframe 328 may convert the cross-EHR instruction to an EHR-specific instruction that can be executed over EHR System 320, and forward the EHR-specific action to Message Bus 314, which may enable to execute the action such as by forwarding the action to EHR DOM API 312.

In some exemplary embodiments, any other configuration may be utilized. For example, instead of implementing Runtime Iframe 328 differently for each EHR system, Runtime Iframe 328 may be implemented in a single form for multiple EHR systems that may have a similar syntax. In such cases, Extension 330 may not necessarily be required to contact Extending Service 340 prior to loading Runtime Iframe 328. In some cases, in case of a single Runtime Iframe 328, Extension 330 may contact Extending Service 340 prior to loading Runtime Iframe 328 such as in order to obtain updated versions of Runtime Iframe 328, of URLs of the Runtime Iframe 328 or applications, of Extension 330, or the like. In some cases, any other widget may be used instead of iframes, in case they enable to load applications therein and communicate with the software agent.

Figure 4:
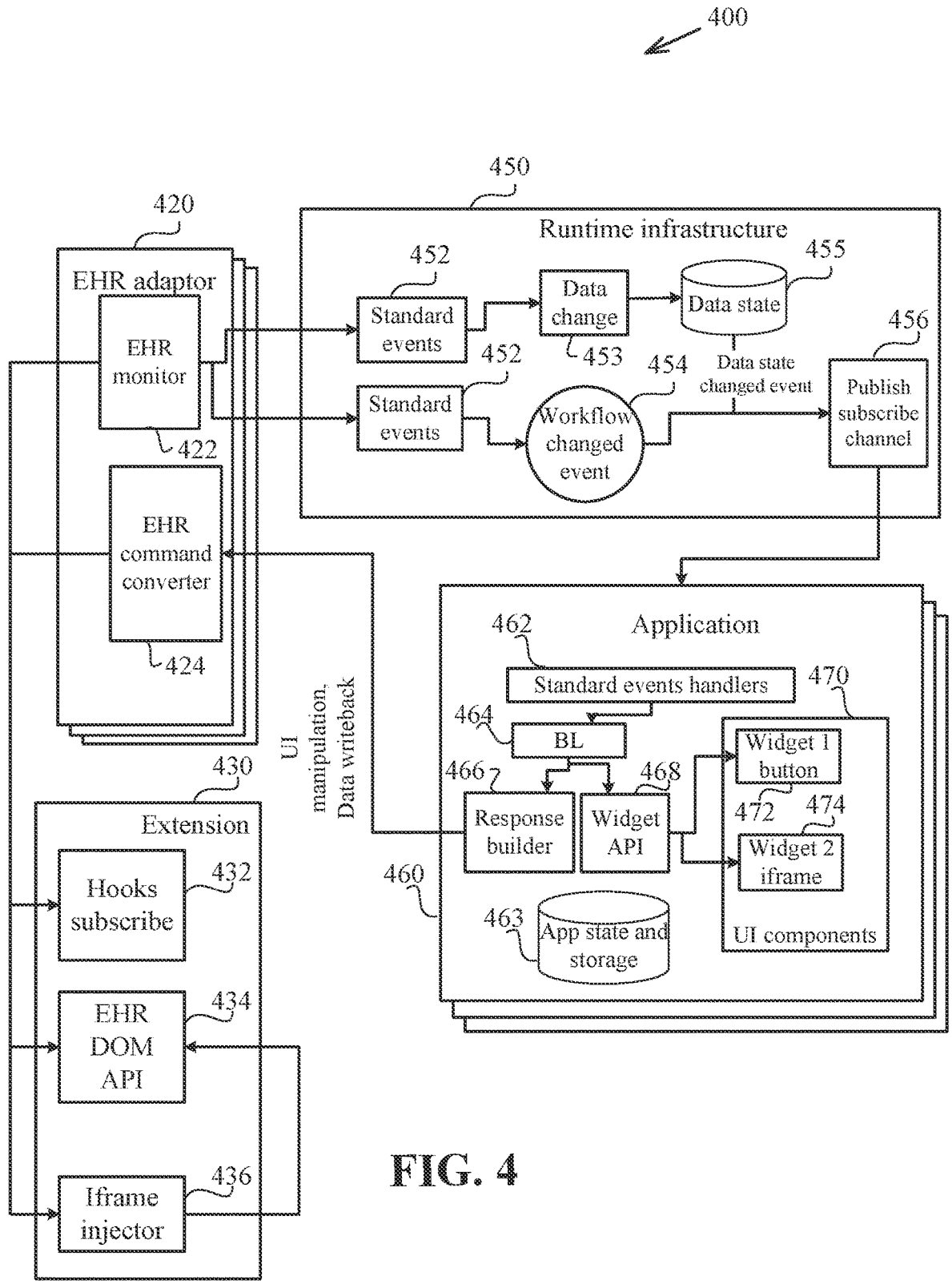
FIG. 4 shows a schematic illustration of an exemplary environment and architecture in which the disclosed subject matter may be utilized, in accordance with some exemplary embodiments of the disclosed subject matter.

Referring now to FIG. 4 showing a schematic illustration of an exemplary environment, in accordance with some exemplary embodiments of the disclosed subject matter.

In some exemplary embodiments, Environment 400 may comprise an Extension 430, which may correspond to Extension 330 (FIG. 3). In some exemplary embodiments, Extension 430 may comprise a Hooks Subscribe 432, an EHR DOM API 434, and an Iframe Injector 436. In some exemplary embodiments, Hooks Subscribe 432 may enable Extension 430 to monitor events using hooks, instead of or in addition to utilizing API calls to obtain EHR elements via EHR DOM API 434.

In some exemplary embodiments, Environment 400 may comprise an EHR Adapter 420 and Runtime Infrastructure 450, which may correspond, together, to Runtime Iframe 328 (FIG. 3). In some exemplary embodiments, EHR Adapter 420 may comprise an EHR Monitor 422 and an EHR Command Converter 424, which may be configured to interpret the DOM of the EHR page, obtain EHR events from Extension 430 and convert the events to a cross-EHR representation, respectively. In some exemplary embodiments, Runtime Infrastructure 450 may obtain cross-EHR Standard Events 452 from EHR Adapter 420, identify whether the events obtained from Extension 430 indicate changes such as a Data Change 453, a new Data State 455, a Workflow Changed Event 454, or the like. In some exemplary embodiments, Runtime Infrastructure 450 may comprise Publish Subscribe Channel 456, which may determine which Applications 460 that are loading in the page are subscribed to one or more of the events or changes, and indicate the events to the applications, e.g., via postMessage communications. For example, an application may be registered to a certain data change, to a certain data state, to a workflow state, or the like.

In some exemplary embodiments, Environment 400 may comprise an Applications 460, which may correspond to the applications loading over Widget Iframes 326 (FIG. 3). In some exemplary embodiments, Applications 460 may comprise a plurality of applications that are configured to be executed in iframes over EHR systems, to provide a functionality in response to an EHR event, or the like. An Application 460 may comprise any augmented functionality or data that is configured to provide augmented functionality over any EHR system, certain types thereof, or the like. Each Application 460 may subscribe to certain data or workflow events in the EHR system, and determine a functionality for the EHR display in case a subscribed event is identified by EHR Adapter 420. In some exemplary embodiments, Applications 460 may comprise applications that are obtained from an open marketplace enabling unauthorized vendors to provide applications, even in case they have no granted access to sensitive or private user data, e.g., PHI data.

In some exemplary embodiments, in order to prevent from Applications 460 to access any PHI data, Applications 460 may only be enabled to communicate with Runtime Infrastructure 450, which may provide thereto cross-EHR non-sensitive information of events that were converted by EHR Adapter 420, without user data. In some exemplary embodiments, only Applications 460 that are registered to a specific event or state may be notified in case such event occurs, which may further limit the access to such events. In some exemplary embodiments, in some cases, Applications 460 may be enabled to provide an offline response, without connecting to a providing server of the application's vendor, thereby further limiting any information about the event that is accessible to the providing server, as the server may not be aware that the response of its application has been executed. Alternatively, Applications 460 may be enabled to provide an online response, utilizing a connection to a providing server. In some exemplary embodiments, Application State and Storage 463 may retain the current state and the storage of the application, which may or may not enable offline event handling.

In some exemplary embodiments, Applications 460 may comprise a Standard Events Handler 462, which may obtain an indicated cross-EHR event from Runtime Infrastructure 450, and provide the event indication to Business Logic (BL) 464. BL 464 may comprise a function, code, or the like, that may be executed in response to the event, in order to determine a response to the event. BL 464 may utilize a Response Builder 466 to generate cross-EHR instructions for execution by Extension 430. Response Builder 466 may forward cross-EHR instructions to EHR Adapter 420, which may convert the instructions to EHR-specific instructions that can be executed over the underlying EHR system by Extension 430. EHR Adapter 420 may provide the converted EHR-specific instructions to Extension 430, which may execute the instructions, implement them, or the like. In case the desired response includes a modification of a UI component in the respective iframe, BL 464 may utilize Widgets API 468 for adding GUI elements to UI Components 470, manipulating UI Components 470, or the like. For example, BL 464 may configure Widgets API 468 to add a Button Widget 472 to the display, to modify an Iframe Widget 474, or the like.

In some exemplary embodiments, Extension 430 may be cross-EHR and cross-application, as it may be used for multiple EHR system and multiple Applications 460, similarly to the underlying operating system being cross-EHR and cross-application. EHR Adapter 420 may not necessarily be cross-EHR, as it may be configured to convert the cross-EHR semantics to EHR-specific semantics of Extension 430, the underlying EHR system, or the like. In some cases, EHR Adapter 420 and Runtime Infrastructure 450 may be tailored to match a specific EHR system, to which and from which the cross-EHR semantics may be converted. In some cases, EHR Adapter 420 may be tailored to match a specific EHR system, while Runtime Infrastructure 450 may match multiple EHR systems, e.g., may be partly reusable.

In some exemplary embodiments, in order for the architecture of Environment 400 to function properly for desktop EHR applications, that are not executed by a browser, EHR Adapter 420 may be replaced with one or more desktop adapters, and Extension 430 may be replaced with a software agent that can be executed over desktop applications, such as a sniffer, a computer vision agent, DLL injections, a WinAPI agent, a reverse engineering agent, or the like.

Figure 5:
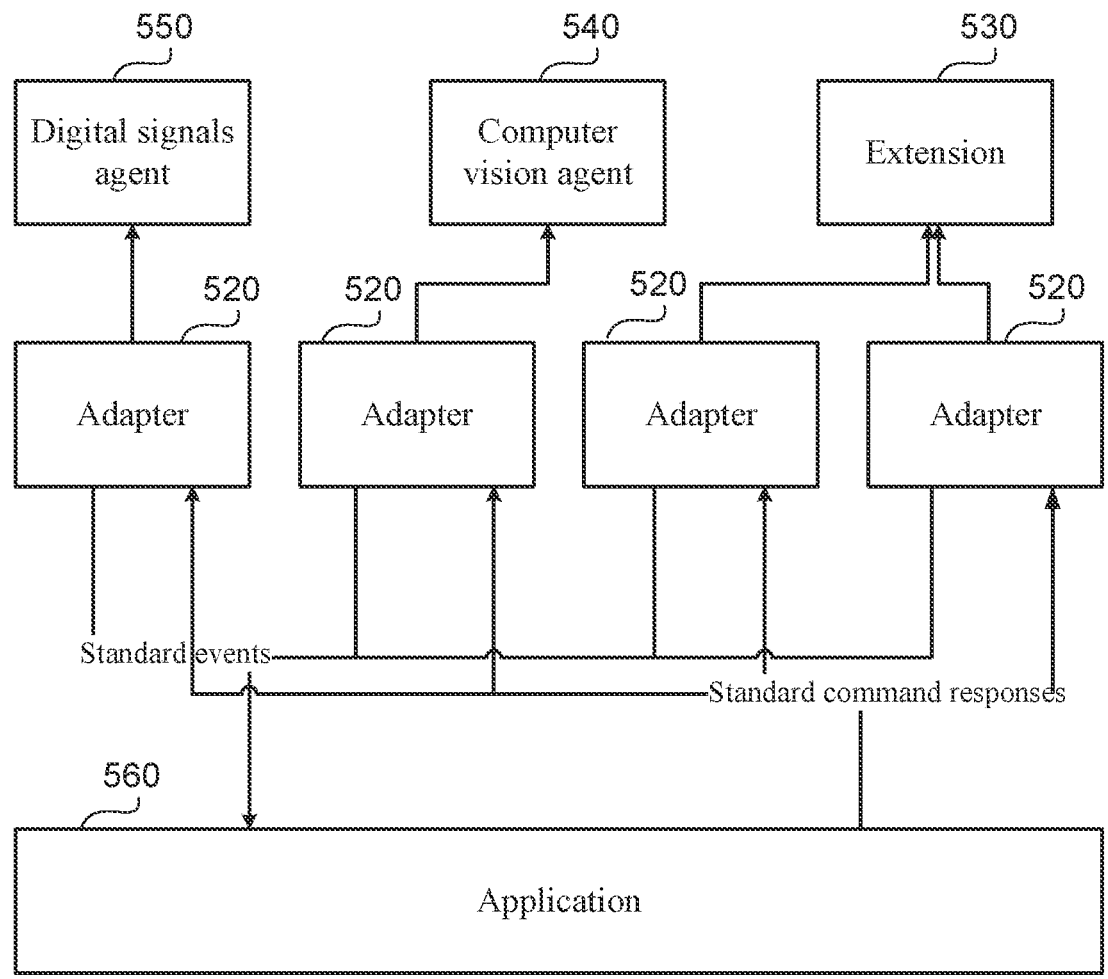
FIG. 5 shows a schematic illustration of an exemplary environment and architecture in which the disclosed subject matter may be utilized, in accordance with some exemplary embodiments of the disclosed subject matter.

Referring now to FIG. 5 showing a schematic illustration of an exemplary environment, in accordance with some exemplary embodiments of the disclosed subject matter.

As illustrated in FIG. 5, one or more agents such as Extension 530, Computer Vision Agent 540, Digital Signals Agents 550, or the like, may be configured to monitor events of an EHR interface. The agents may correspond to Extension 330 (FIG. 3). The identified events may be provided to one or more Adapters 520, which may be configured to standardize the identified events to a normalized language or representation that is used by all applications. Adapters 520 may correspond to Runtime Iframe 328 (FIG. 3). Adapters 520 may determine whether each Application 560 is registered to an event, and in case it is, an Adapter 520 may indicate to Application 560 that the event has occurred, with or without any specific or sensitive information about the event. For example, Adapter 520 may indicate that a type of user interaction has occurred, without indicating which GUI element was interacted with, which user account was activated during the session, or the like.

In some exemplary embodiments, Application 560 may be configured to perform a responsive action such as to load one or more GUI elements, to perform code executions, or the like, over the EHR system, in response to the event. Applications 560 may correspond to Widget Iframes 326 (FIG. 3). In some exemplary embodiments, Application 560 may be configured to determine a responsive action in a cross-EHR format. In some exemplary embodiments, Application 560 may provide the responsive action to one or more Adapters 520, which may convert the responsive action to an EHR-specific command that matches the underlying EHR system that is being used, is launched, is executing, or the like. The EHR-specific command may be provided to an agent such as Extension 530, Computer Vision Agent 540, Digital Signals Agents 550, which may execute the command.

Figure 6:
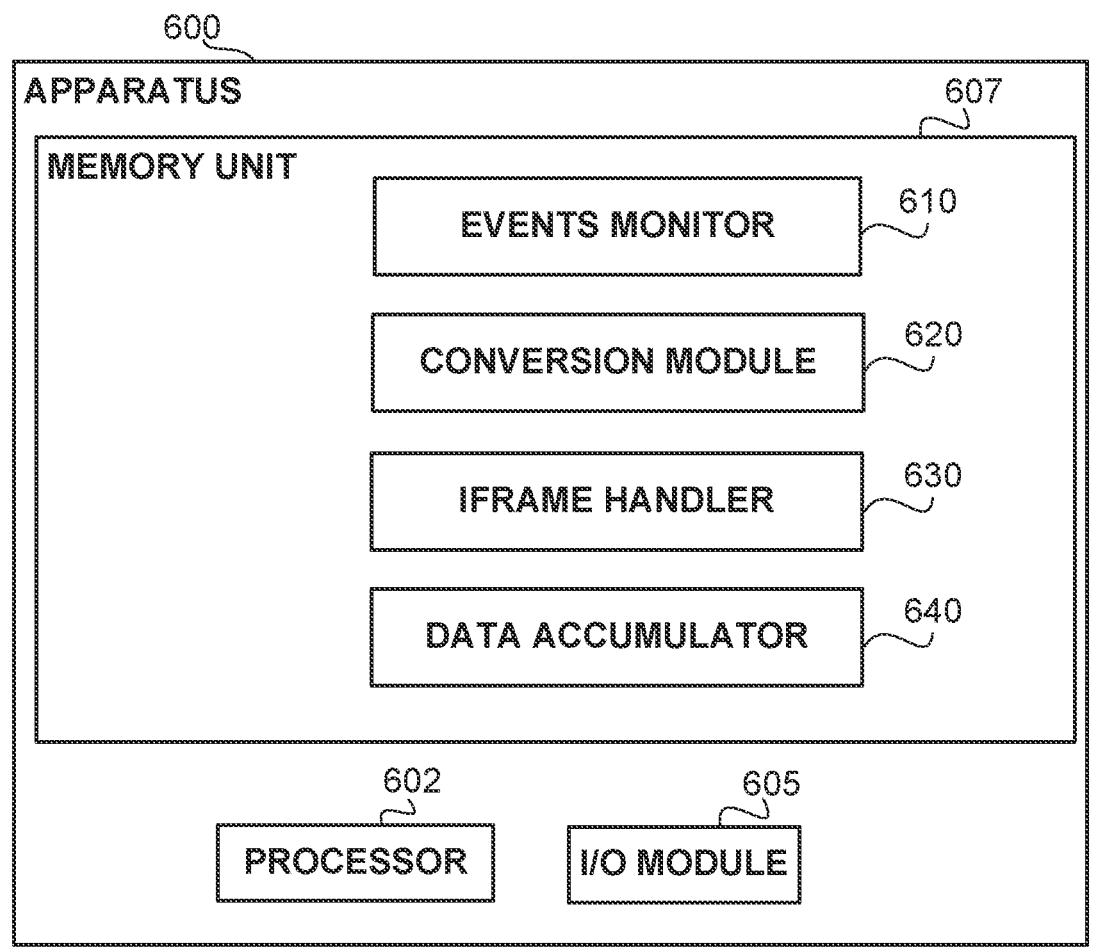
FIG. 6 illustrates a block diagram of an apparatus, in accordance with some exemplary embodiments of the disclosed subject matter.

Referring now to FIG. 6 showing a block diagram of an apparatus, in accordance with some exemplary embodiments of the disclosed subject matter.

In some exemplary embodiments, an Apparatus 600 may comprise a Processor 602. Processor 602 may be a Central Processing Unit (CPU), a microprocessor, an electronic circuit, an Integrated Circuit (IC) or the like. Processor 602 may be utilized to perform computations required by Apparatus 600 or any of its subcomponents. Processor 602 may be configured to execute computer-programs useful in performing the methods of FIGS. 1-2, or the like.

In some exemplary embodiments of the disclosed subject matter, an Input/Output (I/O) Module 605 may be utilized to provide an output to and receive input from a user. I/O Module 605 may be used to transmit and receive information to and from the user or any other apparatus, e.g., a plurality of user devices, in communication therewith.

In some exemplary embodiments, Apparatus 600 may comprise a Memory Unit 607. Memory Unit 607 may be a short-term storage device or long-term storage device. Memory Unit 607 may be a persistent storage or volatile storage. Memory Unit 607 may be a disk drive, a Flash disk, a Random Access Memory (RAM), a memory chip, or the like. In some exemplary embodiments, Memory Unit 607 may retain program code operative to cause Processor 602 to perform acts associated with any of the subcomponents of Apparatus 600. In some exemplary embodiments, Memory Unit 607 may retain program code operative to cause Processor 602 to perform acts associated with any of the steps in FIGS. 1-2, or the like.

The components detailed below may be implemented as one or more sets of interrelated computer instructions, executed for example by Processor 602 or by another processor. The components may be arranged as one or more executable files, dynamic libraries, static libraries, methods, functions, services, or the like, programmed in any programming language and under any computing environment.

In some exemplary embodiments, Events Monitor 610 may be configured to monitor an EHR system that is being executed on a user device, an end device, or the like. Events Monitor 610 may identify one or more events, states, or the like, for which one or more extending applications may be registered, such as using hooks, API calls, or the like. For example, Events Monitor 610 may be part of an agent such as a browser extension, e.g., a CHROME™ browser, a desktop agent, or the like.

In some exemplary embodiments, Conversion Module 620 may be configured to obtain EHR-specific event indications from Events Monitor 610, and convert them to a cross-EHR representation that may be provided to registered applications. Upon obtaining from the registered applications a cross-EHR instruction to perform a responsive action, Conversion Module 620 may be configured to convert the a cross-EHR instruction to an EHR-specific instruction such as an EHR-specific API call to the EHR system.

In some exemplary embodiments, Iframe Handler 630 may comprise runtime infrastructure that is configured to be loaded over a runtime iframe, load Conversion Module 620, and load one or more extending application over widget iframes. In some exemplary embodiments, in case an additional application is intended to be loaded, Iframe Handler 630 may instruct Events Monitor 610 to inject an additional iframe, and load the additional application therein. In some exemplary embodiments, Iframe Handler 630 may be enabled to adjust applications in real time, such as by modifying a URL of an iframe, modifying a source code to which the iframe points, or the like. In some exemplary embodiments, Iframe Handler 630 may communicate with the iframes directly, and provide outputs from the iframes to Conversion Module 620.

In some exemplary embodiments, Data Accumulator 640 may be configured to accumulate data from an EHR system, a DOM thereof, or the like, and provide the data to a storage of the extending service. For example, Data Accumulator 640 may obtain state indications, event indications, screenshots, or the like, from Events Monitor 610.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An apparatus comprising:
a processor, and
a memory,
wherein said memory retaining a browser extension that is configured, when executed by said processor, to monitor and interact with a Document Object Model (DOM) of a page of an Electronic Health Record (EHR) system, wherein the browser extension is configured to be executed by a browser, wherein the browser is configured to render the page of the EHR system;
a runtime infrastructure that is loaded, dynamically, in the page of the EHR system in a first iframe, wherein the runtime infrastructure lacks a Graphical User Interface (GUI) representation;
an EHR-specific EHR adapter that is loaded, dynamically, in the page of the EHR system; and
an extending application that is loaded, dynamically, in the page of the EHR system in a second iframe,
wherein the browser extension is configured to inject the first iframe in the page of the EHR system and cause the runtime infrastructure to be loaded into the first iframe, wherein the browser extension is configured to inject the second iframe in the page of the EHR system and enable the runtime infrastructure to load the extending application into the second iframe,
wherein the EHR-specific EHR adapter is specifically designed based on the EHR system, wherein the EHR-specific EHR adapter is configured to receive EHR-specific instructions from the browser extension and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the browser extension,
wherein said apparatus is configured to implement a functionality that is not provided by the EHR system at least by:
monitoring, by the browser extension, for an event in the EHR system;
notifying, by the browser extension, the EHR-specific EHR adapter of the event via an EHR-specific instruction;
translating, by the EHR-specific EHR adapter, the EHR-specific instruction to a converted cross-EHR instruction that is provided to the extending application via the runtime infrastructure;
executing, by the extending application, a cross-EHR business logic in response to the converted cross-EHR instruction to determine a cross-EHR response; and
translating, by the EHR-specific EHR adapter, the cross-EHR response to a converted EHR-specific instruction that can be implemented by the browser extension over the EHR system.

2. The apparatus of claim 1, wherein the extending application comprises a GUI component, wherein the business logic is configured to manipulate the GUI component.

3. The apparatus of claim 1, wherein the extending application is an automation process, wherein the automation process lacks a GUI representation.

4. The apparatus of claim 1, wherein the runtime infrastructure is configured to: retrieve from a server a list of applications to be loaded in the page, wherein the list of applications to be loaded comprises at least the extending application, wherein the runtime infrastructure is configured to dynamically load the extending application in the second iframe by provisioning a Uniform Resource Locator (URL) to be loaded in the second iframe, wherein the URL is pointing to a code of the extending application, whereby the apparatus is enabled to load new code and provision new functionality by changing the code or changing the URL without changing the browser extension, whereby the apparatus prevents a dynamic execution of a string representing client-side code.

5. The apparatus of claim 4, wherein the list of applications to be loaded is determined based on access permissions of a user of the EHR system to applications in an application repository.

6. The apparatus of claim 1, wherein the cross-EHR response is configured to perform a User Interface (UI) manipulation in the page of the EHR system or a data update in the page of the EHR system.

7. The apparatus of claim 1, wherein the browser extension is configured to inject the EHR-specific EHR adapter in the page of the EHR system and load the EHR-specific EHR adapter.

8. The apparatus of claim 1, wherein the runtime infrastructure is configured to retrieve from a server a list of applications to be loaded in the page, wherein the list of applications to be loaded comprises the extending application and a second application, wherein the extending application belongs to a first organization associated with a first server, wherein the second application belongs to a second organization associated with a second server, wherein the runtime infrastructure is configured to dynamically load the second application in a third iframe embedded in the page by provisioning a Uniform Resource Locator (URL) to be loaded in the third iframe, wherein the URL is pointing to a code of the second application.

9. The apparatus of claim 1, wherein the runtime infrastructure is configured to retrieve from a server a list of applications to be loaded in the page, wherein the list of applications to be loaded comprises the extending application and a second application, wherein the extending application belongs to a first organization associated with a first server, wherein the second application belongs to a second organization associated with a second server, wherein the runtime infrastructure is configured to dynamically load the second application in the second iframe by provisioning a Uniform Resource Locator (URL) of the second application to be loaded in the second iframe, wherein the URL of the second application is pointing to a code of the second application, wherein the URL of the second application replaces a URL of the extending application.

10. The apparatus of claim 9, wherein the runtime infrastructure is configured to dynamically load the second application in the second iframe in response to a second event.

11. The apparatus of claim 1, wherein a list of applications is available in a marketplace, wherein any provider is enabled to upload a new application to the marketplace, wherein a user of the EHR system is enabled to install in a user device any application from the marketplace.

12. The apparatus of claim 1, wherein the EHR-specific EHR adapter is configured to indicate to the browser extension an element of interest via an indication, wherein the browser extension is configured to monitor the element of interest in response to the indication, wherein the browser extension is configured to notify the EHR-specific EHR adapter of the EHR-specific instruction in response to monitoring the event, wherein the event is associated to the element of interest.

13. The apparatus of claim 1, wherein the browser extension is configured to inject the first and second iframes in response to determining that the extending application is configured to be loaded over the page of the EHR system.

14. A computer program product comprising a non-transitory computer readable medium retaining program instructions, which program instructions when read by a processor, cause the processor to:
monitor and interact with a Document Object Model (DOM) of a page of an Electronic Health Record (EHR) system using a browser extension, wherein the browser extension is configured to be executed by a browser, wherein the browser is configured to render the page of the EHR system;
dynamically load a runtime infrastructure in the page of the EHR system in a first iframe, wherein the runtime infrastructure lacks a Graphical User Interface (GUI) representation;
dynamically load an EHR-specific EHR adapter in the page of the EHR system; and
dynamically load an extending application in the page of the EHR system in a second iframe,
wherein the browser extension is configured to inject the first iframe in the page of the EHR system and cause the runtime infrastructure to be loaded into the first iframe, wherein the browser extension is configured to inject the second iframe in the page of the EHR system and enable the runtime infrastructure to load the extending application into the second iframe,
wherein the EHR-specific EHR adapter is specifically designed based on the EHR system, wherein the EHR-specific EHR adapter is configured to receive EHR-specific instructions from the browser extension and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the browser extension,
wherein said processor is configured to implement a functionality that is not provided by the EHR system at least by:
monitoring, by the browser extension, for an event in the EHR system;
notifying, by the browser extension, the EHR-specific EHR adapter of the event via an EHR-specific instruction;
translating, by the EHR-specific EHR adapter, the EHR-specific instruction to a converted cross-EHR instruction that is provided to the extending application via the runtime infrastructure;
executing, by the extending application, a cross-EHR business logic in response to the converted cross-EHR instruction to determine a cross-EHR response; and
translating, by the EHR-specific EHR adapter, the cross-EHR response to a converted EHR-specific instruction that can be implemented by the browser extension over the EHR system.

15. A method comprising:
monitoring and interacting with a Document Object Model (DOM) of a page of an Electronic Health Record (EHR) system using a browser extension, wherein the browser extension is configured to be executed by a browser, wherein the browser is configured to render the page of the EHR system;
dynamically loading a runtime infrastructure in the page of the EHR system in a first iframe, wherein the runtime infrastructure lacks a Graphical User Interface (GUI) representation;
dynamically loading an EHR-specific EHR adapter in the page of the EHR system; and
dynamically loading an extending application in the page of the EHR system in a second iframe,
wherein the browser extension is configured to inject the first iframe in the page of the EHR system and cause the runtime infrastructure to be loaded into the first iframe, wherein the browser extension is configured to inject the second iframe in the page of the EHR system and enable the runtime infrastructure to load the extending application into the second iframe,
wherein the EHR-specific EHR adapter is specifically designed based on the EHR system, wherein the EHR-specific EHR adapter is configured to receive EHR-specific instructions from the browser extension and communicate converted cross-EHR instructions to the runtime infrastructure, wherein the runtime infrastructure is configured to communicate the converted cross-EHR instructions to the extending application, wherein the runtime infrastructure is configured to receive cross-EHR instructions from the extending application, wherein the EHR-specific EHR adapter is configured to obtain the cross-EHR instructions and communicate converted EHR-specific instructions to the browser extension,
wherein a processor is configured to implement a functionality that is not provided by the EHR system at least by:
monitoring, by the browser extension, for an event in the EHR system;
notifying, by the browser extension, the EHR-specific EHR adapter of the event via an EHR-specific instruction;
translating, by the EHR-specific EHR adapter, the EHR-specific instruction to a converted cross-EHR instruction that is provided to the extending application via the runtime infrastructure;

executing, by the extending application, a cross-EHR business logic in response to the converted cross-EHR instruction to determine a cross-EHR response; and translating, by the EHR-specific EHR adapter, the cross-EHR response to a converted EHR-specific instruction that can be implemented by the browser extension over the EHR system.

16. The method of claim 15, wherein the extending application comprises a GUI component, wherein the business logic is configured to manipulate the GUI component.

17. The method of claim 15, wherein the extending application is an automation process, wherein the automation process lacks a GUI representation.

18. The method of claim 15 further comprising: retrieving from a server, by the runtime infrastructure, a list of applications to be loaded in the page, wherein the list of applications to be loaded comprises at least the extending application, and dynamically loading, by the runtime infrastructure, the extending application in the second iframe by provisioning a Uniform Resource Locator (URL) to be loaded in the second iframe, wherein the URL is pointing to a code of the extending application, whereby the processor is enabled to load new code and provision new functionality by changing the code or changing the URL without changing the browser extension, whereby the processor prevents a dynamic execution of a string representing client-side code.

19. The method of claim 18 further comprising determining the list of applications to be loaded based on access permissions of a user of the EHR system to applications in an application repository.

20. The method of claim 15 further comprising indicating, by the EHR-specific EHR adapter, an element of interest via an indication to the browser extension, wherein the method further comprises monitoring the element of interest, by the browser extension, in response to the indication, wherein the method further comprises notifying, by the browser extension, the EHR-specific EHR adapter of the EHR-specific instruction in response to monitoring the event, wherein the event is associated to the element of interest.

* * * * *